US009706932B2

(12) United States Patent
McCulloch et al.

(10) Patent No.: US 9,706,932 B2
(45) Date of Patent: Jul. 18, 2017

(54) CUFF FOR A BLOOD PRESSURE MEASURING SYSTEM

(75) Inventors: Robert T. McCulloch, Macomb, MI (US); Jerome Joler, Rochester Hills, MI (US); Matthew William Vergin, Anderson, SC (US)

(73) Assignee: FKA Distributing Co., LLC, Commerce Township, MI (US)

( * ) Notice: Subject to any disclaimer, the term of this patent is extended or adjusted under 35 U.S.C. 154(b) by 955 days.

(21) Appl. No.: 13/576,021

(22) PCT Filed: Jan. 31, 2011

(86) PCT No.: PCT/US2011/023177
§ 371 (c)(1),
(2), (4) Date: Dec. 14, 2012

(87) PCT Pub. No.: WO2011/094688
PCT Pub. Date: Aug. 4, 2011

(65) Prior Publication Data
US 2013/0123649 A1     May 16, 2013

Related U.S. Application Data

(60) Provisional application No. 61/300,185, filed on Feb. 1, 2010.

(51) Int. Cl.
*A61B 5/02*     (2006.01)
*A61B 5/022*     (2006.01)

(52) U.S. Cl.
CPC ................. *A61B 5/02233* (2013.01)

(58) Field of Classification Search
CPC .................................................. A61B 5/0223

USPC .................................................. 600/490–499
See application file for complete search history.

(56) References Cited

U.S. PATENT DOCUMENTS

| 1,809,278 | A | * | 6/1931 | Kestenman | A44C 5/24 |
| | | | | | 224/176 |
| 3,696,469 | A | * | 10/1972 | Kalinsky | 24/71 J |
| 4,353,374 | A | * | 10/1982 | Rebbe et al. | 600/499 |
| 5,188,115 | A | * | 2/1993 | Otani | 600/490 |
| 5,351,694 | A | * | 10/1994 | Davis | A61B 5/02241 |
| | | | | | 600/485 |
| 6,308,382 | B1 | * | 10/2001 | Takahashi | A44C 5/24 |
| | | | | | 24/265 WS |
| 2007/0271747 | A1 | * | 11/2007 | Yamamoto | A44C 5/246 |
| | | | | | 24/71 J |

(Continued)

FOREIGN PATENT DOCUMENTS

| DE | EP 1013220 | * | 6/2000 | ............ A61B 5/022 |
| EP | 1013220 | | 6/2000 | |
| GB | 1450322 | | 9/1976 | |

OTHER PUBLICATIONS

International Search Report and Written Opinion for PCT/US2011/023177 dated Mar. 25, 2011.

*Primary Examiner* — Tiffany Weston
(74) *Attorney, Agent, or Firm* — Brooks Kushman P.C.

(57) ABSTRACT

A cuff for a blood pressure measuring system including a flexible elongate band having a first end and a second end and a sizing mechanism coupled to the band, wherein the sizing mechanism selectively permits relative movement between the first end and the second end of the band to expand and constrict a diameter of the band.

7 Claims, 12 Drawing Sheets

(56) References Cited

U.S. PATENT DOCUMENTS

2009/0199367 A1\* 8/2009 Fuhrman .............. A44C 5/2076
24/303

\* cited by examiner

CUFF FOR A BLOOD PRESSURE MEASURING SYSTEM

CROSS-REFERENCE TO RELATED APPLICATION

This application is the U.S. national phase of PCT Appln. No. PCT/US2011/023177 filed on Jan. 31, 2011, which claims the benefit of U.S. provisional application Ser. No. 61/300,185 filed on Feb. 1, 2010, the disclosures of which are incorporated in their entirety by reference herein.

FIELD OF THE INVENTION

The invention relates to a blood pressure measuring system, and more particularly to a cuff for a blood pressure measuring system having a sizing mechanism.

BACKGROUND OF THE INVENTION

Blood within a body of a person is characterized by a systolic and diastolic blood pressure. Non-invasive systems for measuring the systolic and diastolic blood pressure include an auscultation measuring system and an oscillometric measuring system, for example. Both the auscultation measuring system and the oscillometric measuring system utilize an inflatable cuff. The systems depend in part on a size of the cuff relative to a size of an arm of the person whose blood pressure is being measured. Inaccuracies in the blood pressure measurement can result if the cuff is improperly sized.

With the rise in home healthcare, the number of patients required to conduct routine blood pressure measurements at home has significantly increased. Typically, the blood pressure measurements are conducted by patients of varying age and sophistication. Prior art systems for measuring blood pressure include a cuff that is wrapped around an arm of the patient reaching an arbitrary tightness thereof. The tightness of the cuff influences the blood pressure measurement. Thus, variability of the tightness of the cuff for each blood pressure measurement can result in inaccuracies.

It would be desirable to produce a cuff for a blood pressure measuring system, which is simple to use and facilitates accurate blood pressure measurements.

SUMMARY OF THE INVENTION

In concordance and agreement with the present invention, a cuff for a blood pressure measuring system, which is simple to use and facilitates accurate blood pressure measurements, has surprisingly been discovered.

In one embodiment, the cuff for a blood pressure measuring system comprises: a flexible elongate band including a first end and a second end; and a sizing mechanism coupled to at least one of the first end and the second end of the band, wherein the sizing mechanism selectively expands and constricts a diameter of the band.

In another embodiment, the cuff for a blood pressure measuring system comprises: a flexible elongate band including a first end and a second end; and a sizing mechanism coupled to at least one of the first end and the second end of the band, the sizing mechanism including a plurality of linkages and a clasping mechanism pivotally coupled to at least one of the linkages, wherein at least one of the linkages is affixed to at least one of the first end and the second end of the band, and wherein the sizing mechanism selectively expands and constricts a diameter of the band.

In another embodiment, the cuff for a blood pressure measuring system comprises: a flexible elongate band including a first end and a second end, wherein a first portion of one of the first end and the second end of the band formed from an affixing material cooperates with a second portion of the one of the first end and the second end of the band formed from an affixing material; and a sizing mechanism coupled to at least one of the first end and the second end of the band, wherein the sizing mechanism selectively expands and constricts a diameter of the band.

DESCRIPTION OF THE DRAWINGS

The above, as well as other advantages of the present invention will become readily apparent to those skilled in the art from the following detailed description of a preferred embodiment when considered in the light of the accompanying drawings in which.

DESCRIPTION OF THE PREFERRED EMBODIMENTS

The following detailed description and appended drawings describe and illustrate various exemplary embodiments of the invention. The description and drawings serve to enable one skilled in the art to make and use the invention, and are not intended to limit the scope of the invention in any manner.

Figure 1:
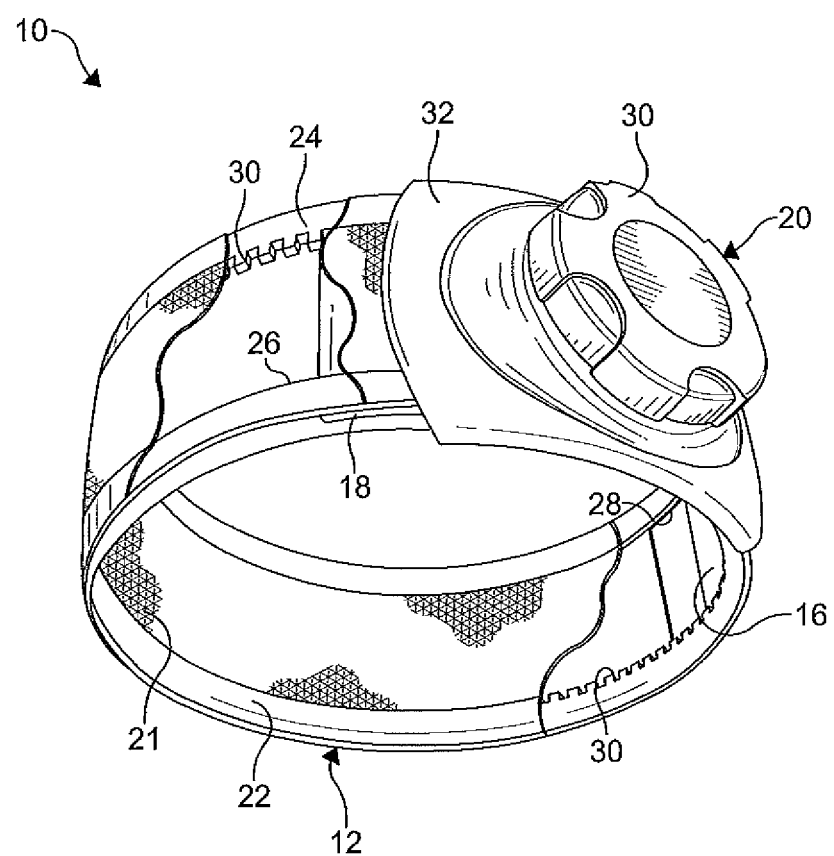
FIG. 1 is a bottom perspective view of a cuff for a blood pressure measuring system according to an embodiment of the invention with portions thereof cutaway.

FIG. 1 shows a cuff 10 for a blood pressure measuring system (not shown) according to an embodiment of the invention. The cuff 10 includes a flexible elongate band 12 having spaced apart opposing ends 16, 18 and a sizing feature or mechanism 20. It is understood that the band 12 can have any length as desired. The band 12 includes an inner surface 22 and an outer surface 24. In the embodiment shown, the end 16 is caused to overlap the end 18 to form a loop. A cover 21 may be disposed around the band 12 such that the overlapping ends 16, 18 of the band 12 are within the cover 21. It is understood that the cover 21 may be formed from any material as desired such as a mesh material, for example. The ends 16, 18 include respective elongate openings 26, 28 formed therein. It is understood that the opening 26 can be formed integral with the opening 28 if desired. Each of the openings 26, 28 includes a plurality of teeth 30 laterally extending from an inner surface thereof. Alternatively, the openings 26, 28 may include other configurations such as a plurality of slots or upstanding ribs, for example, formed generally perpendicular to a longitudinal axis of the band 12. The band 12 may include a surface treatment such as a lubricating coating, for example, to minimize a coefficient of friction to facilitate relative movement of adjacent surfaces of the ends 16, 18 during use.

The sizing mechanism 20 is operably coupled to the ends 16, 18 for effecting relative movement therebetween to selectively constrict or expand a diameter of the cuff 10. It is understood, however, that the sizing mechanism 20 can be fixedly coupled to one of the ends 16, 18 if desired. The sizing mechanism 20 includes an actuator 30 rotatably mounted in a receiving element 32. In the embodiment shown, the actuator 30 is a rotatable knob coupled to a gear having a plurality of teeth formed thereon. The teeth of the gear engage and cooperate with the teeth 30 formed on the inner surfaces of the openings 26, 28 to effect relative movement between the ends 16, 18. A passageway (not shown) formed in the receiving element 32 receives the ends 16, 18 of the band 12 therein.

In operation, the ends 16, 18 of the band 12 are inserted into the passageway formed in the receiving element 32 of the sizing mechanism 20. An arm of a user is then inserted through the loop formed by the band 12. The actuator 30 is then rotated to cause the teeth of the gear to cooperate with the teeth 30 of openings 26, 28. When the actuator 30 is rotated in a first direction, the ends 16, 18 of the band 12 are urged in a first opposite direction causing the outer surface 24 of the end 18 of the band 12 to slideably travel along the inner surface 22 of the end 16 and constrict a diameter of the cuff 10 until a desired diameter of the cuff 10 is reached.

After a blood pressure measurement is conducted by the blood pressure measuring system, the actuator 30 is urged outward away from the band 12 causing the cuff 10 to loosen from around the arm of the user. Particularly, when the actuator 30 is urged outward, the teeth of the gear disengage the teeth 30 formed on the openings 26, 28. Accordingly, the ends 16, 18 of the band 12 are free to move in a second opposite direction causing the outer surface 24 of the end 18 of the band 12 to slideably retract along the inner surface 22 of the end 16 of the band 12 and expand the diameter of the cuff 10. The receiving element 32 of the sizing mechanism 20 guides the movement of the ends 16, 18 of the band 12.

Figure 2:
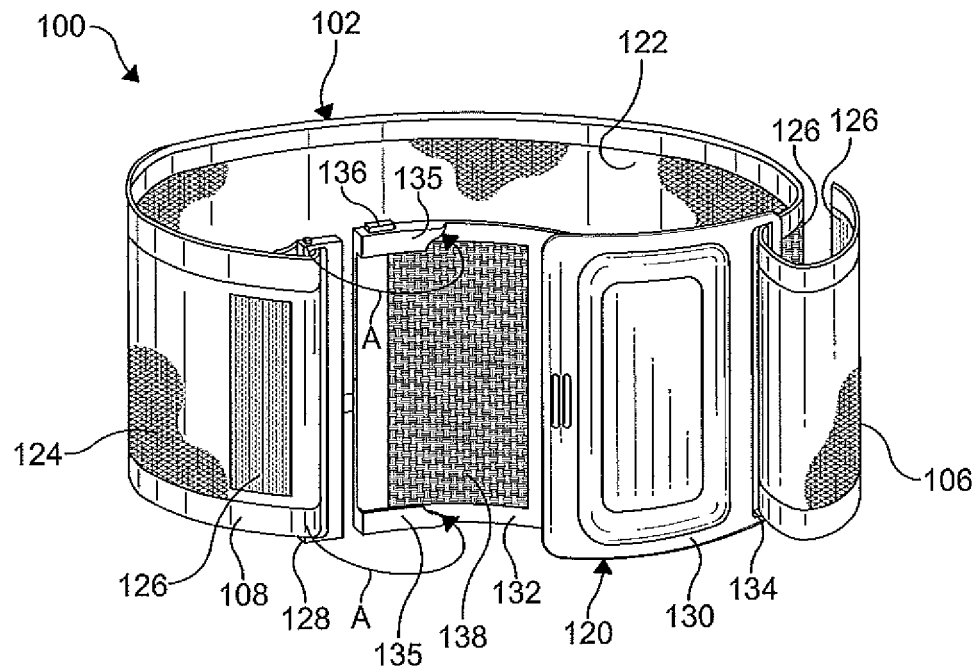
FIG. 2 is a top perspective view of a cuff for a blood pressure measuring system according to another embodiment of the invention, wherein the cuff is in an extended position.
Figure 3:
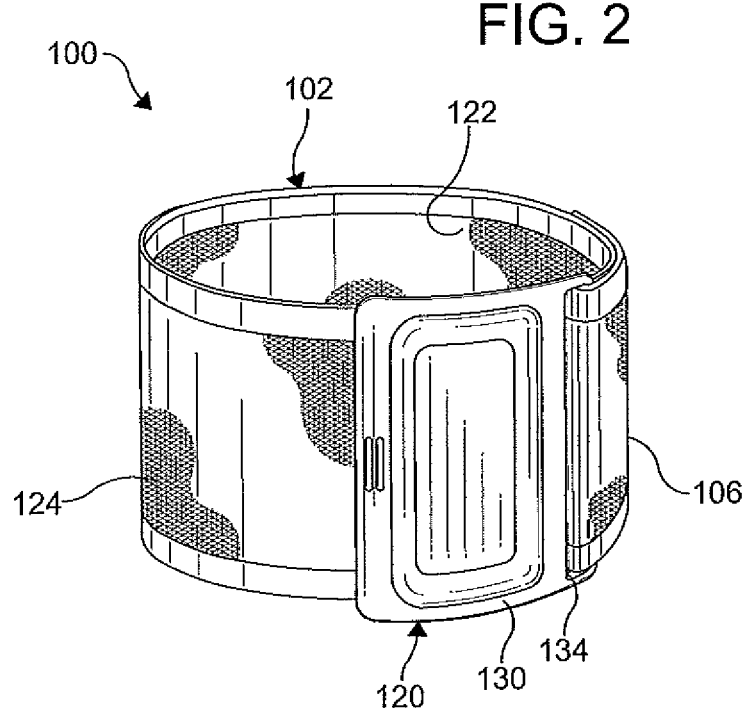
FIG. 3 is a top perspective view of the cuff for a blood pressure measuring system illustrated in FIG. 2, wherein the cuff is in a retracted position.

FIGS. 2-3 show a cuff 100 for a blood pressure measuring system (not shown) according to another embodiment of the invention. The cuff 100 includes a flexible elongate band 102 having spaced apart opposing ends 106, 108 and a sizing feature or mechanism 120. It is understood that the band 102 can have any length as desired. The band 102 includes an inner surface 122 and an outer surface 124. As illustrated in FIG. 2, portions of the outer surface 124 are produced from an affixing material 126 such as hook and loop tape, for example. It is understood, however, that the band 102 can be produced from any material as desired. An attachment device 128 is disposed on the end 108 of the band 102. It is understood that the attachment device 128 can be disposed on the end 106 if desired.

As illustrated, the sizing mechanism 120 includes a clasping mechanism 130. A slot 134 for receiving one of the ends 106, 108 therethrough is formed in the clasping mechanism 130. The clasping mechanism 130 shown is pivotally coupled to a linkage 132. The linkage 132 is pivotable between a first or extended position, as shown in FIG. 2, and a second or retracted position, as shown in FIG. 3. The linkage 132 includes a pair of spaced apart receiving elements 135 adapted to receive the attachment device 128 therein. Actuators 136 such as push buttons, for example, are disposed in the linkage 132 for releasing the attachment device 128 therefrom. As shown, the linkage 132 includes an affixing material 138 such as hook and loop tape, for example, disposed on a surface thereof. It is understood that the clasping mechanism 130 and the linkage 132 may further include corresponding features such as ribs and grooves, for example, formed thereon to militate against an undesired movement therebetween.

In operation, the linkage 132 of the sizing mechanism 120 is positioned in the extended position. The end 108 of the band 102, including the attachment device 128, is then disposed in the receiving elements 135 thereof as indicated by the arrows A in FIG. 2. The linkage 132 is pivoted to the retracted position causing the clasping mechanism 130 to be positioned on a portion of the end 108 of the band 102 having the linkage 132 disposed therebetween. The affixing material 138 of the linkage 132 cooperates with the affixing material 126 of the band 102 to releasably secure the sizing mechanism 120 to the band 102. Thereafter, a first portion of the end 106 of the band 102 is disposed through the slot 134 of the clasping mechanism 130. The first portion of the end 106 of the band 102 is caused to overlap onto a second portion of the end 106 of the band 102 to form a loop and constrict a diameter of the cuff 100. The diameter of the cuff 100 is constricted until a desired diameter of the cuff 100 is reached. The affixing material 126 disposed on the first portion of the end 106 cooperates with the affixing material 126 disposed on the second portion of the end 106 to maintain the desired diameter of the cuff 100.

After a blood pressure measurement is conducted by the blood pressure measuring system, the linkage 132 of the sizing mechanism 120 is pivoted to the extended position, separating the affixing material 138 of the linkage 132 from the affixing material 126 of the end 108 and expanding the diameter of the cuff 100. Once the desired diameter of the cuff 100 is determined during a first blood pressure measurement, the sizing mechanism 120 can be used to expand and constrict the diameter of the cuff 100. The affixing material 126 disposed on the first portion of the end 106 remains in cooperation with the affixing material 126 disposed on the second portion of the end 106 until an adjustment to the desired diameter of the cuff 100 is needed. Further, the actuators 136 may be activated to release the attachment device 128 disposed on the end 108 from the linkage 132 of the sizing mechanism 120.

Figure 4:
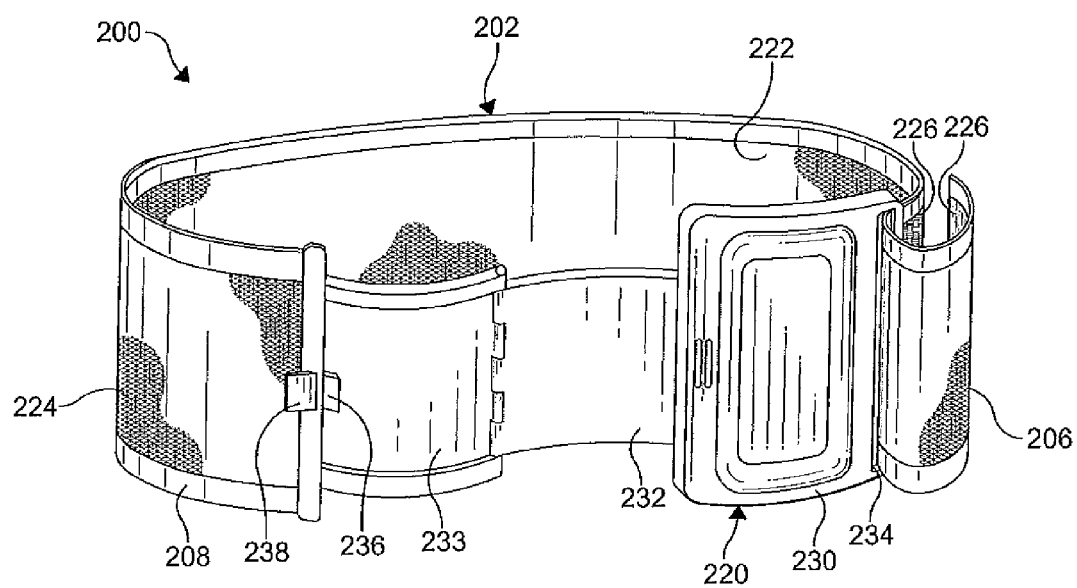
FIG. 4 is a top perspective view of a cuff for a blood pressure measuring system according to another embodiment of the invention, wherein the cuff is in an extended position.
Figure 5:
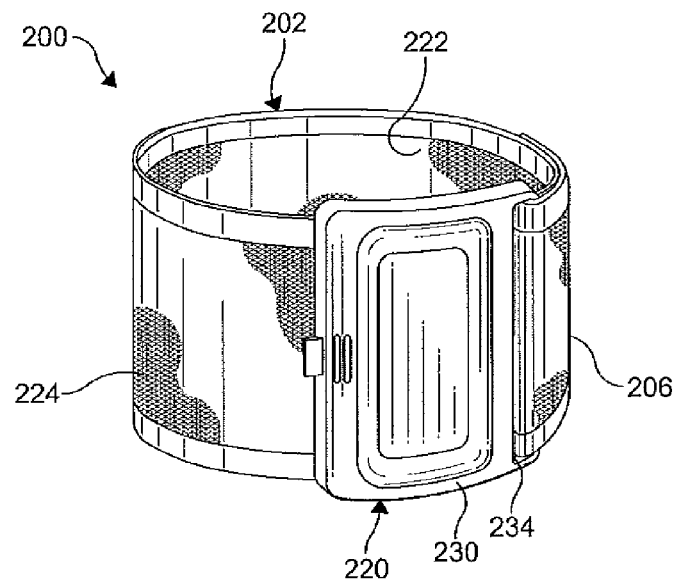
FIG. 5 is a top perspective view of the cuff for a blood pressure measuring system illustrated in FIG. 4, wherein the cuff is in a retracted position.

FIGS. 4-5 show a cuff 200 for a blood pressure measuring system (not shown) according to another embodiment of the invention. The cuff 200 includes a flexible elongate band 202 having spaced apart opposing ends 206, 208 and a sizing feature or mechanism 220. It is understood that the band 202 can have any length as desired. The band 202 includes an inner surface 222 and an outer surface 224. As illustrated in FIG. 4, portions of the outer surface 224 are produced from an affixing material 226 such as hook and loop tape, for example. It is understood, however, that the band 202 can be produced from any material as desired.

As shown, the sizing mechanism 220 includes a clasping mechanism 230 and a pair of linkages 232, 233. It is understood that the sizing mechanism 220 can be produced from any material as desired such as a plastic material, for example. A slot 234 for receiving one of the ends 206, 208 therethrough is formed in the clasping mechanism 230. The clasping mechanism 230 is pivotally coupled to the linkage 232. The linkage 232 is pivotable between a first or extended position, as shown in FIG. 4, and a second or retracted position, as shown in FIG. 5. The linkage 232 is pivotally coupled to the linkage 233. The linkage 233 is coupled to one of the ends 206, 208 of the band 202. It is understood that the linkage 233 can be coupled to one of the ends 206, 208 as desired such as by an attachment mechanism, adhesive, and any combination thereof, for example. As shown, the linkage 233 includes a protuberance 236 formed thereon. The protuberance 236 cooperates with the clasping mechanism 230 to form an interference fit therebetween. A pivotable mechanism 238 is coupled to the protuberance 236 to cause a release of the clasping mechanism 230 therefrom. It is understood that the clasping mechanism 230 and the linkages 232, 233 may further include corresponding features such as ribs and grooves, for example, formed thereon to militate against an undesired movement therebetween.

In operation, the linkage 232 of the sizing mechanism 220 is positioned in the retracted position. The clasping mechanism 230 is then urged in a first direction and positioned on the linkage 233 having the linkage 232 disposed therebetween. The protuberance 236 of the linkage 233 cooperates with the clasping mechanism 230 to form the interference fit therebetween and releasably secure the sizing mechanism 220 in a closed position as shown in FIG. 5. Thereafter, a first portion of the end 206 of the band 202 is disposed through the slot 234 of the clasping mechanism 230. The first portion of the end 206 of the band 202 is caused to overlap onto a second portion of the end 206 of the band 202 to form a loop and constrict a diameter of the cuff 200. The diameter of the cuff 200 is constricted until a desired diameter of the cuff 200 is reached. The affixing material 226 disposed on the first portion of the end 206 cooperates with the affixing material 226 disposed on the second portion of the end 206 to maintain the desired diameter of the cuff 200.

After a blood pressure measurement is conducted by the blood pressure measuring system, the clasping mechanism 230 of the sizing mechanism 220 is urged outward away from the band 202 by the pivotable mechanism 238. The clasping mechanism 230 is then urged in a second direction causing a pivoting of the linkage 232 to the extended position and expanding the diameter of the cuff 200. Once the desired diameter of the cuff 200 is determined during a first blood pressure measurement, the sizing mechanism 220 can be used to expand and constrict the diameter of the cuff 200. The affixing material 226 disposed on the first portion of the end 206 remains in cooperation with the affixing material 226 disposed on the second portion of the end 206 until an adjustment to the desired diameter of the cuff 200 is needed.

Figure 6:
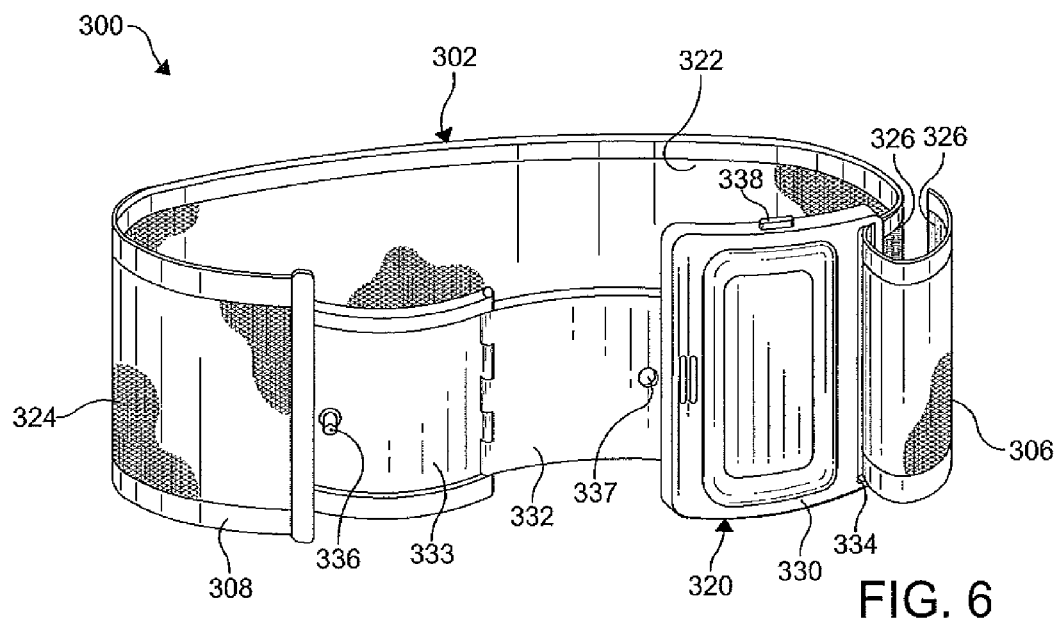
FIG. 6 is a top perspective view of a cuff for a blood pressure measuring system according to another embodiment of the invention, wherein the cuff is in an extended position.
Figure 7:
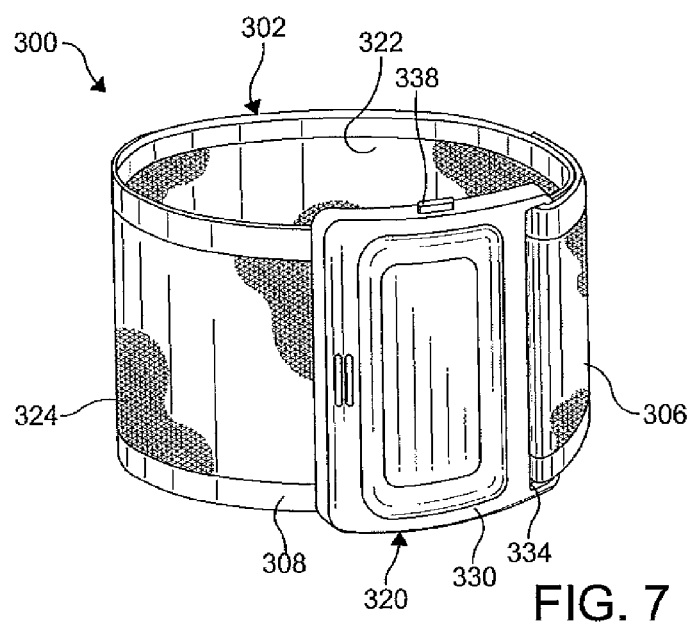
FIG. 7 is a top perspective view of the cuff for a blood pressure measuring system illustrated in FIG. 6, wherein the cuff is in a retracted position.

FIGS. 6-7 show a cuff 300 for a blood pressure measuring system (not shown) according to another embodiment of the invention. The cuff 300 includes a flexible elongate band 302 having spaced apart opposing ends 306, 308 and a sizing feature or mechanism 320. It is understood that the band 302 can have any length as desired. The band 302 includes an inner surface 322 and an outer surface 324. As illustrated in FIG. 6, portions of the outer surface 324 are produced from an affixing material 326 such as hook and loop tape, for example. It is understood, however, that the band 302 can be produced from any material as desired.

As shown, the sizing mechanism 320 includes a clasping mechanism 330 and a pair of linkages 332, 333. It is understood that the sizing mechanism 320 can be produced from any material as desired such as a plastic material, for example. A slot 334 for receiving one of the ends 306, 308 therethrough is formed in the clasping mechanism 330. The clasping mechanism 330 is pivotally coupled to the linkage 332. The linkage 332 is pivotable between a first or extended position, as shown in FIG. 6, and a second or retracted position, as shown in FIG. 7. The linkage 332 is pivotally coupled to the linkage 333. The linkage 333 is coupled to one of the ends 306, 308 of the band 302. It is understood that the linkage 333 can be coupled to one of the ends 306, 308 as desired such as by an attachment mechanism, adhesive, and any combination thereof, for example. As shown, the linkage 333 includes a protuberance 336 formed thereon. An aperture (not shown) formed in the clasping mechanism 330 and an aperture 337 formed in the linkage 332 receives the protuberance 336 therethrough. The protuberance 336 is releasably secured in the clasping mechanism 330 by a receiving element (not shown) disposed in the clasping mechanism 330. The clasping mechanism 330 includes an actuator 338 such as a push button, for example, to cause the receiving element to release the protuberance 336 therefrom. It is understood that the clasping mechanism 330 and the linkages 332, 333 may further include corresponding features such as ribs and grooves, for example, formed thereon to militate against an undesired movement therebetween.

In operation, the linkage 332 is positioned in the retracted position. The clasping mechanism 330 is then urged in a first direction and positioned on the linkage 333 having the linkage 332 disposed therebetween. The protuberance 336 of the linkage 333 is received through the aperture 337 formed in the linkage 332, through the aperture formed in the clasping mechanism 330, and into the receiving element disposed in the clasping mechanism 330 to releasably secure the sizing mechanism 320 in a closed position as shown in FIG. 7. Thereafter, a first portion of the end 306 of the band 302 is disposed through the slot 334 of the clasping mechanism 330. The first portion of the end 306 of the band 302 is caused to overlap onto a second portion of the end 306 of the band 302 to form a loop and constrict a diameter of the cuff 300. The diameter of the cuff 300 is constricted until a desired diameter of the cuff 300 is reached. The affixing material 326 disposed on the first portion of the end 306 cooperates with the affixing material 326 disposed on the second portion of the end 306 to maintain the desired diameter of the cuff 300.

After a blood pressure measurement is conducted by the blood pressure measuring system, the actuator 338 is activated, thereby releasing the protuberance 336 from the receiving element. The clasping mechanism 330 of the sizing mechanism 320 is then urged outward away from the band 302. The clasping mechanism 330 is then urged in a second direction causing a pivoting of the linkage 332 to the extended position and expanding the diameter of the cuff 300. Once the desired diameter of the cuff 300 is determined during a first blood pressure measurement, the sizing mechanism 320 can be used to expand and constrict the diameter of the cuff 300. The affixing material 326 disposed on the first portion of the end 306 remains in cooperation with the affixing material 326 disposed on the second portion of the end 306 until an adjustment to the desired diameter of the cuff 300 is needed.

Figure 8:
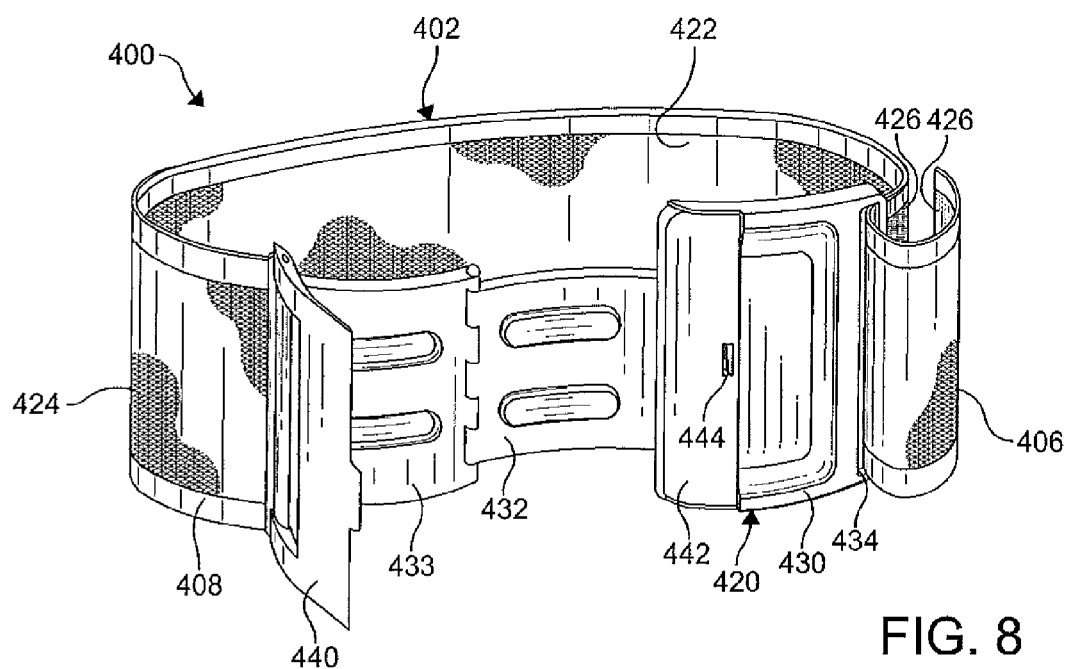
FIG. 8 is a top perspective view of a cuff for a blood pressure measuring system according to another embodiment of the invention, wherein the cuff is in an extended position.
Figure 9:
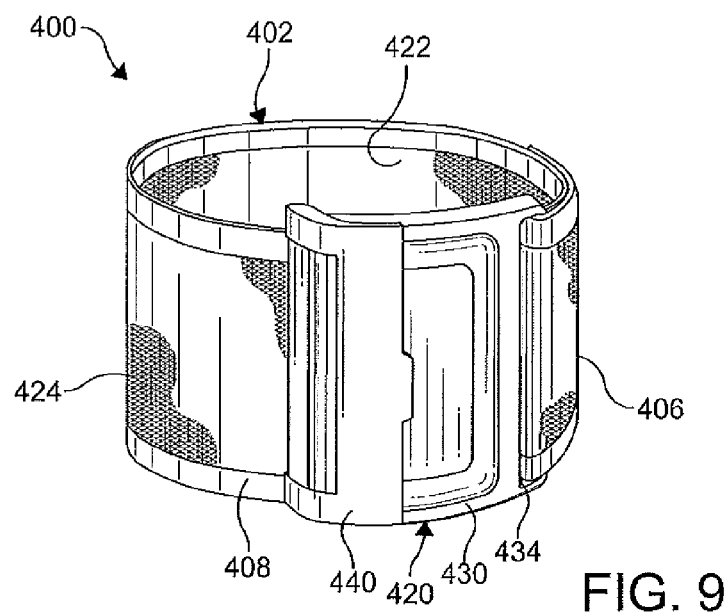
FIG. 9 is a top perspective view of the cuff for a blood pressure measuring system illustrated in FIG. 8, wherein the cuff is in a retracted position.

FIGS. 8-9 show a cuff 400 for a blood pressure measuring system (not shown) according to another embodiment of the invention. The cuff 400 includes a flexible elongate band 402 having spaced apart opposing ends 406, 408 and a sizing feature or mechanism 420. It is understood that the band 402 can have any length as desired. The band 402 includes an inner surface 422 and an outer surface 424. As illustrated in FIG. 8, portions of the outer surface 424 are produced from an affixing material 426 such as hook and loop tape, for example. It is understood, however, that the band 402 can be produced from any material as desired.

As shown, the sizing mechanism 420 includes a clasping mechanism 430 and a pair of linkages 432, 433. It is understood that the sizing mechanism 420 can be produced from any material as desired such as a plastic material, for example. A slot 434 for receiving one of the ends 406, 408 therethrough is formed in the clasping mechanism 430. The clasping mechanism 430 is pivotally coupled to the linkage 432. The linkage 432 is pivotable between a first or extended position, as shown in FIG. 8, and a second or retracted position, as shown in FIG. 9. The linkage 432 is pivotally coupled to the linkage 433. The linkage 433 is coupled to one of the ends 406, 408 of the band 402. It is understood that the linkage 433 can be coupled to one of the ends 406, 408 as desired such as by an attachment mechanism, adhesive, and any combination thereof, for example. As shown, the linkage 433 includes a protuberance (not shown) formed thereon. The protuberance cooperates with the clasping mechanism 430 to form an interference fit therebetween. The linkage 433 further includes a latch 440 pivotally coupled thereto. The latch 440 is received in a corresponding indentation 442 formed in the clasping mechanism 430. The latch 440 includes a protuberance (not shown) formed thereon. An aperture 444 formed in the clasping mechanism 430 receives the protuberance therein to form an interference fit between the latch 440 and the clasping mechanism 430. It is understood that the clasping mechanism 430 and the linkages 432, 433 may further include corresponding features such as ribs and grooves, for example, formed thereon to militate against an undesired movement therebetween.

In operation, the linkage 432 is positioned in the retracted position. The clasping mechanism 430 is then urged in a first direction and positioned on the linkage 433 having the linkage 432 disposed therebetween. The protuberance of the linkage 433 cooperates with the clasping mechanism 430 to form the interference fit therebetween and releasably secure the sizing mechanism 420 in a closed position as shown in FIG. 9. Thereafter, the latch 440 is urged in a first direction and positioned in the indentation 442 formed in the clasping mechanism 430. The protuberance of the latch 440 is received in the aperture 444 of the clasping mechanism 430 forming the interference fit therebetween and further securing the sizing mechanism 420 in the closed position. A first portion of the end 406 of the band 402 is then disposed through the slot 434 of the clasping mechanism 430. The first portion of the end 406 of the band 402 is caused to overlap onto a second portion of the end 406 of the band 402 to form a loop and constrict a diameter of the cuff 400. The diameter of the cuff 400 is constricted until a desired diameter of the cuff 400 is reached. The affixing material 426 disposed on the first portion of the end 406 cooperates with the affixing material 426 disposed on the second portion of the end 406 to maintain the desired diameter of the cuff 400.

After a blood pressure measurement is conducted by the blood pressure measuring system, the latch 440 is urged in a second direction releasing the protuberance formed thereon from the aperture 444 formed in the clasping mechanism 430 of the sizing mechanism 420. Thereafter, the clasping mechanism 430 is urged outward away from the band 402 releasing the clasping mechanism 430 from the protuberance formed on the linkage 433. The clasping mechanism 430 is then urged in a second direction causing a pivoting of the linkage 432 to the extended position and expanding the diameter of the cuff 400. Once the desired diameter of the cuff 400 is determined during a first blood pressure measurement, the sizing mechanism 420 can be used to expand and constrict the diameter of the cuff 400. The affixing material 426 disposed on the first portion of the end 406 remains in cooperation with the affixing material 426 disposed on the second portion of the end 406 until an adjustment to the desired diameter of the cuff 400 is needed.

Figure 10:
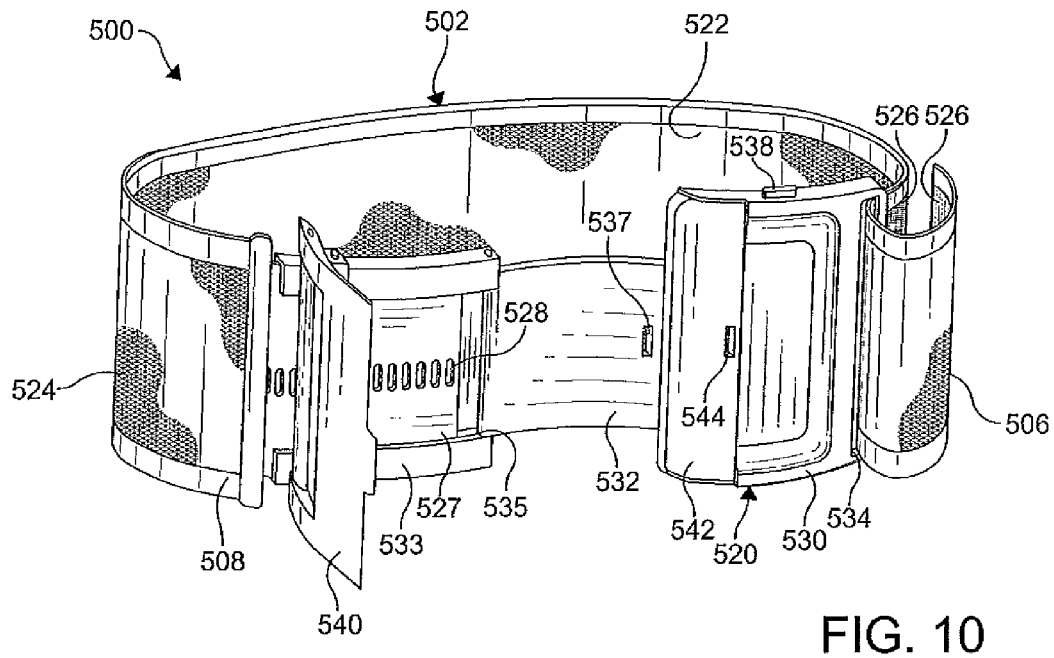
FIG. 10 is a top perspective view of a cuff for a blood pressure measuring system according to another embodiment of the invention, wherein the cuff is in an extended position.
Figure 11:
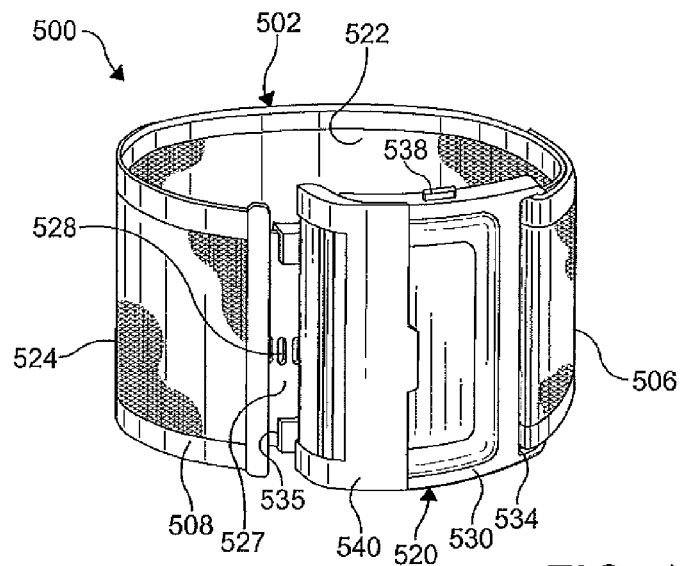
FIG. 11 is a top perspective view of the cuff for a blood pressure measuring system illustrated in FIG. 10, wherein the cuff is in a retracted position.

FIGS. 10-11 show a cuff 500 for a blood pressure measuring system (not shown) according to another embodiment of the invention. The cuff 500 includes a flexible elongate band 502 having spaced apart opposing ends 506, 508 and a sizing feature or mechanism 520. It is understood that the band 502 can have any length as desired. The band 502 includes an inner surface 522 and an outer surface 524. As illustrated in FIG. 10, portions of the outer surface 524 are produced from an affixing material 526 such as hook and loop tape, for example. It is understood, however, that the band 502 can be produced from any material as desired. In the embodiment shown, the end 508 includes an adjustment portion 527 having a plurality of slots 528 formed generally perpendicular to the longitudinal axis of the band 502. It is understood that the slots 528 can be other configurations as desired such as ribs, detents, teeth, and the like, for example. It is further understood that the adjustment portion 527 can be affixed to the end 508 if desired by any method such as by an attachment device, adhesive, fasteners, and any combination thereof, for example.

As shown, the sizing mechanism 520 includes a clasping mechanism 530 and a pair of linkages 532, 533. It is understood that the sizing mechanism 520 can be produced from any material as desired such as a plastic material, for example. A slot 534 for receiving the end 506 therethrough is formed in the clasping mechanism 530. The clasping mechanism 530 is pivotally coupled to the linkage 532. The linkage 532 is pivotable between a first or extended position, as shown in FIG. 10, and a second or retracted position, as shown in FIG. 11. The linkage 532 is pivotally coupled to the linkage 533.

The linkage 533 is coupled to the adjustment portion 527 of the end 508 of the band 502. In the embodiment shown, the linkage 533 includes a pair of spaced apart channels 535 and a detent (not shown) formed thereon. The channels 535 are spaced apart to receive the linkage 532 therebetween when the linkage 532 is in the retracted position. The channels 535 slideably receive the adjustment portion 527 therein and guide a movement thereof during use. The detent of the linkage 533 cooperates with one of the slots 528 formed in the adjustment portion 527 to releasably secure the adjustment portion 527 therein. The linkage 533 further includes a protuberance (not shown) formed thereon. An aperture (not shown) formed in the clasping mechanism 530 and an aperture 537 formed in the linkage 532 receive the protuberance therethrough when the sizing mechanism 520 is in a closed position as shown in FIG. 11. The protuberance is releasably secured in the clasping mechanism 530 by a receiving element (not shown) disposed therein. The clasping mechanism 530 includes an actuator 538 such as a push button, for example, to cause the receiving element to release the protuberance therefrom.

As illustrated, a latch 540 is pivotally coupled to the linkage 533. The latch 540 is received in a corresponding indentation 542 formed in the clasping mechanism 530. The latch 540 includes a protuberance (not shown) formed thereon. An aperture 544 formed in the clasping mechanism 530 receives the protuberance therein to form an interference fit between the latch 540 and the clasping mechanism 530. It is understood that the clasping mechanism 530 and the linkages 532, 533 may further include corresponding features such as ribs and grooves, for example, formed thereon to militate against an undesired movement therebetween.

In operation, the linkage 532 is pivoted to the expanded position. Thereafter, the adjustment portion 527 of the end 508 of the band 502 is inserted into the channels 535 formed on the linkage 533 of the sizing mechanism 520. The adjustment portion 527 is urged in a first direction causing an inner surface thereof to slideably travel along an outer surface of the linkage 533 and constrict a diameter of the cuff 500 until a desired position is reached. The decent formed on the linkage 533 cooperates with one of the slots 528 formed in the adjustment portion 527 to releasably secure the end 508 of the band 502 at the desired position.

The clasping mechanism 530 is then urged in a first direction and positioned on the linkage 533 further constricting the cuff 500. The linkage 532 is disposed between the clasping mechanism 530 and the linkage 533. The protuberance of the linkage 533 is received through the aperture 537 formed in the linkage 532, through the aperture formed in the clasping mechanism 530, and into the receiving element disposed in the clasping mechanism 530 to releasably secure the sizing mechanism 520 in the closed position. Thereafter, the latch 540 is urged in a first direction and positioned in the indentation 542 formed in the clasping mechanism 530. The protuberance of the latch 540 is received in the aperture 544 of the clasping mechanism 530 forming the interference fit therebetween and further securing the sizing mechanism 520 in the closed position. A first portion of the end 506 of the band 502 is then disposed through the slot 534 of the clasping mechanism 530. The first portion of the end 506 of the band 502 is caused to overlap onto a second portion of the end 506 of the band 502 to form a loop and further constrict the diameter of the cuff 500. The diameter of the cuff 500 is constricted until a desired diameter of the cuff 500 is reached. The affixing material 526 disposed on the first portion of the end 506 cooperates with the affixing material 526 disposed on the second portion of the end 506 to maintain the desired diameter of the cuff 500.

After a blood pressure measurement is conducted by the blood pressure measuring system, the latch 540 is urged in a second direction releasing the protuberance formed thereon from the aperture 544 formed in the clasping mechanism 530 of the sizing mechanism 520. Thereafter, the clasping mechanism 530 is urged outward away from the band 502 releasing the clasping mechanism 530 from the protuberance formed on the linkage 533. The clasping mechanism 530 is then urged in a second direction causing a pivoting of the linkage 532 to the extended position and expanding the diameter of the cuff 500. Once the desired diameter of the cuff 500 is determined during a first blood pressure measurement, the sizing mechanism 520 can be used to expand and constrict the diameter of the cuff 500. The affixing material 526 disposed on the first portion of the end 506 remains in cooperation with the affixing material 526 disposed on the second portion of the end 506 until an adjustment to the desired diameter of the cuff 500 is needed.

Figure 12:
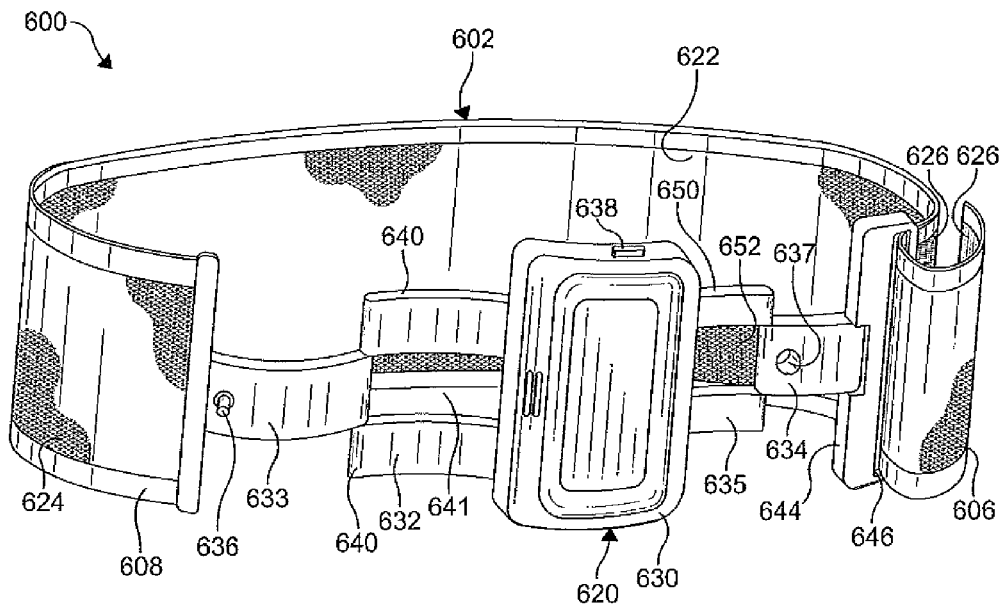
FIG. 12 is a top perspective view of a cuff for a blood pressure measuring system according to another embodiment of the invention, wherein the cuff is in an extended position.
Figure 13:
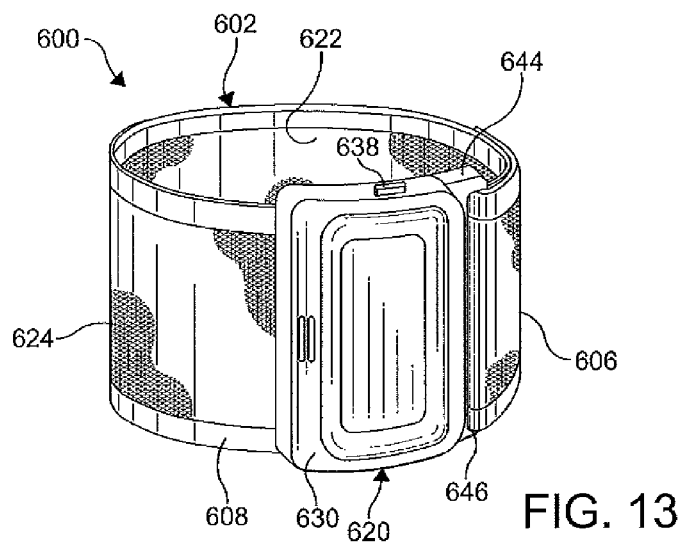
FIG. 13 is a top perspective view of the cuff for a blood pressure measuring system illustrated in FIG. 12, wherein the cuff is in a retracted position.

FIGS. 12-13 show a cuff 600 for a blood pressure measuring system (not shown) according to another embodiment of the invention. The cuff 600 includes a flexible elongate band 602 having spaced apart opposing ends 606, 608 and a sizing feature or mechanism 620. It is understood that the band 602 can have any length as desired. The band 602 includes an inner surface 622 and an outer surface 624. As illustrated in FIG. 12, portions of the outer surface 624 are produced from an affixing material 626 such as hook and loop tape, for example. It is understood, however, that the band 602 can be produced from any material as desired.

As shown, the sizing mechanism 620 includes a clasping mechanism 630 and linkages 632, 633, 634, 635. It is understood that the sizing mechanism 620 can be produced from any material as desired such as a plastic material, for example. The clasping mechanism 630 is pivotally coupled to the linkage 632 and the linkage 635. The linkage 632 is pivotable between a first or extended position, as shown in FIG. 12, and a second or retracted position, as shown in FIG. 13. The linkage 632 includes a pair of spaced apart members 640 defining an opening 641 therebetween. The linkage 632 is pivotally coupled to the linkage 633. The opening 641 of the linkage 632 receives the linkage 633 therein when the sizing mechanism 620 is in a closed position as shown in FIG. 13. The linkage 633 is coupled to one of the ends 606, 608 of the band 602. It is understood that the linkage 633 can be coupled to one of the ends 606, 608 as desired such as by an attachment mechanism, adhesive, and any combination thereof, for example. As shown, the linkage 633 includes a protuberance 636 formed thereon. An aperture (not shown) formed in the clasping mechanism 630 and an aperture 637 formed in the linkage 634 receive the protuberance 636 therethrough when the sizing mechanism 620 is in the closed position. The protuberance 636 is releasably secured in the clasping mechanism 630 by a receiving element (not shown) disposed in the clasping mechanism 630. The clasping mechanism 630 includes an actuator 638 such as a push button, for example, to cause the receiving element to release the protuberance 636 therefrom. As illustrated, the linkage 634 is pivotally coupled to an attachment device 644. The attachment device 644 includes a slot 646 formed therein to receive one of the ends 606, 608 therethrough. The linkage 634 is also pivotally coupled to the linkage 635. The linkage 635 is pivotable between a first or extended position, as shown in FIG. 12, and a second or retracted position, as shown in FIG. 13. The linkage 635 includes a pair of spaced apart members 650 defining and opening 652 therebetween. The opening 652 receives the linkage 634 therein when the sizing mechanism 620 is in the closed position. It is understood that the clasping mechanism 630 and the linkages 632, 633, 634, 635 may further include corresponding features such as ribs and grooves, for example, formed thereon to militate against an undesired movement therebetween.

In operation, the linkage 635 is positioned in the retracted position. The clasping mechanism 630 is then urged in a first direction and positioned on the linkage 634 causing the linkage 634 to pivot and be received into the opening 652 formed in the linkage 635. The aperture 637 is substantially aligned with the aperture formed in the clasping mechanism 630. Thereafter, the linkage 632 is pivoted to the retracted position. The clasping mechanism 630 is then urged in an opposite second direction and positioned on the linkage 633 causing the linkage 633 to pivot and be received into the opening 641 of the linkage 632. The protuberance 636 of the linkage 633 is then received through the aperture 637 formed in the linkage 634 and through the aperture formed in the clasping mechanism 630, and into the receiving element disposed in the clasping mechanism 630 to releasably secure the sizing mechanism 620 in the closed position as shown in FIG. 13. Thereafter, a first portion of the end 606 of the band 602 is disposed through the slot 646 of the attachment device 644. The first portion of the end 606 of the band 602 is caused to overlap onto a second portion of the end 606 of the band 602 to form a loop and constrict a diameter of the cuff 600. The diameter of the cuff 600 is constricted until a desired diameter of the cuff 600 is reached. The affixing material 626 disposed on the first portion of the end 606 cooperates with the affixing material 626 disposed on the second portion of the end 606 to maintain the desired diameter of the cuff 600.

After a blood pressure measurement is conducted by the blood pressure measuring system, the actuator 638 is activated, thereby releasing the protuberance 636 from the receiving element. The clasping mechanism 630 of the sizing mechanism 620 is then urged in the first direction causing a pivoting of the linkage 632 to the extended position and expanding the diameter of the cuff 600. The clasping mechanism 630 is then urged in the second direction causing a pivoting of the linkage 635 to the extended position and further expanding the diameter of the cuff 600. Once the desired diameter of the cuff 600 is determined during a first blood pressure measurement, the sizing mechanism 620 can be used to expand and constrict the diameter of the cuff 600. The affixing material 626 disposed on the first portion of the end 606 remains in cooperation with the affixing material 626 disposed on the second portion of the end 606 until an adjustment to the desired diameter of the cuff 600 is needed.

Figure 14:
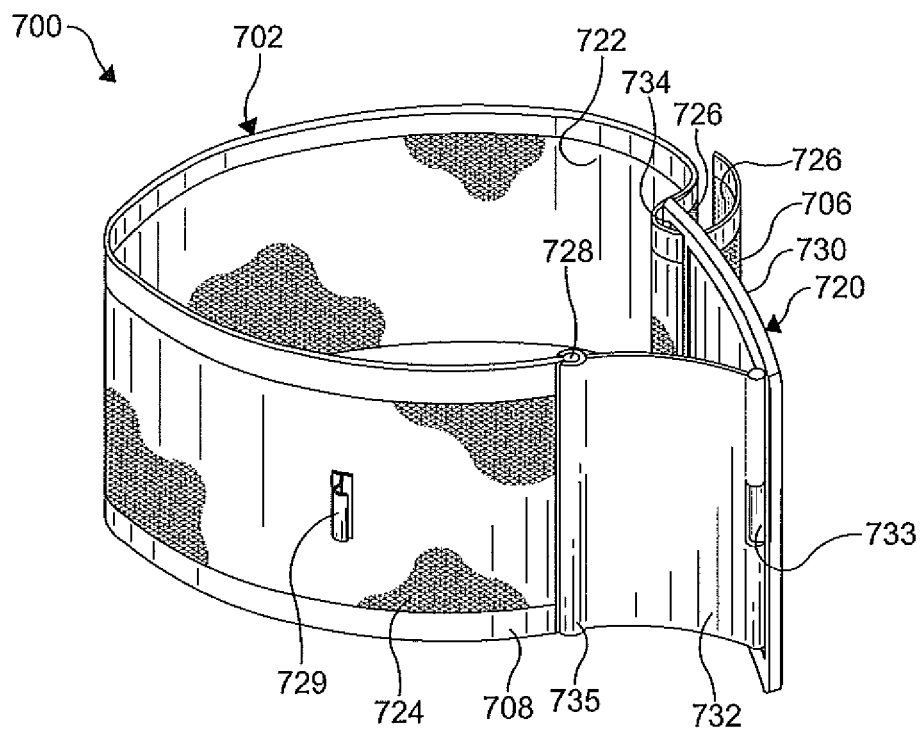
FIG. 14 is a top perspective view of a cuff for a blood pressure measuring system according to another embodiment of the invention, wherein the cuff is in a partially extended position.

FIG. 14 shows a cuff 700 for a blood pressure measuring system (not shown) according to another embodiment of the invention. The cuff 700 includes a flexible elongate band 702 having spaced apart opposing ends 706, 708 and a sizing feature or mechanism 720. It is understood that the band 702 can have any length as desired. The band 702 includes an inner surface 722 and an outer surface 724. Portions of the outer surface 724 are produced from an affixing material 726 such as hook and loop tape, for example. It is understood, however, that the band 702 can be produced from any material as desired. An attachment device 728 is disposed on the end 708 of the band 702. The end 708 of the band 702 further includes a protuberance 729 disposed thereon. It is understood that the attachment device 728 and the protuberance 729 can be disposed on the end 706 of the band 702 if desired. Although the protuberance 729 shown has a generally C-shaped cross-section, it is understood that the protuberance 729 can have any cross-sectional shape as desired such as an S-shaped cross-section, for example. An arcuate outer surface of the protuberance 729 faces away from the sizing mechanism 720.

The sizing mechanism 720 includes a clasping mechanism 730 pivotally coupled to a linkage 732. In the embodiment shown, the clasping mechanism 730 is pivotally coupled to the linkage 732 by a hinge 733. The hinge 733 cooperates with the protuberance 729 disposed on the end 708 of the band 702 to form an interference fit therebetween. Particularly, the protuberance 729 receives the hinge 733 therein. The clasping mechanism 730 includes a slot 734 formed therein for receiving the end 706 of the band 702 therethrough. It is understood that the end 708 of the band 702 can be disposed through the slot 734 if desired. The linkage 732 shown is pivotable between a first or extended position and a second or retracted position. The linkage 732 includes a receiving portion 735 formed thereon. The receiving portion 735 is pivotally coupled to the attachment device 728 disposed on the end 708 of the band 702 to secure the sizing mechanism 720 to the band 702. It is understood that the clasping mechanism 730 and the linkage 732 may further include corresponding features such as ribs and grooves, for example, formed thereon to militate against an undesired movement therebetween.

In operation, the linkage 732 of the sizing mechanism 720 is pivoted to the retracted position causing the clasping mechanism 730 to be positioned on a portion of the end 708 of the band 702 having the linkage 732 disposed therebetween. The hinge 733 is received in the protuberance 729 to form the interference fit therebetween and releasably secure the sizing mechanism 720 in a closed position. Thereafter, a first portion of the end 706 of the band 702 is disposed through the slot 734 of the clasping mechanism 730. The first portion of the end 706 of the band 702 is caused to overlap onto a second portion of the end 706 of the band 702 to form a loop and constrict a diameter of the cuff 700. The diameter of the cuff 700 is constricted until a desired diameter of the cuff 700 is reached. The affixing material 726 disposed on the first portion of the end 706 cooperates with the affixing material 726 disposed on the second portion of the end 706 to maintain the desired diameter of the cuff 700.

After a blood pressure measurement is conducted by the blood pressure measuring system, the linkage 732 of the sizing mechanism 720 is pivoted to the extended position, separating the hinge 733 from the protuberance 729 and expanding the diameter of the cuff 700. Once the desired diameter of the cuff 700 is determined during a first blood pressure measurement, the sizing mechanism 720 can be used to expand and constrict the diameter of the cuff 700. The affixing material 726 disposed on the first portion of the end 706 remains in cooperation with the affixing material 726 disposed on the second portion of the end 706 until an adjustment to the desired diameter of the cuff 700 is needed.

Figure 15:
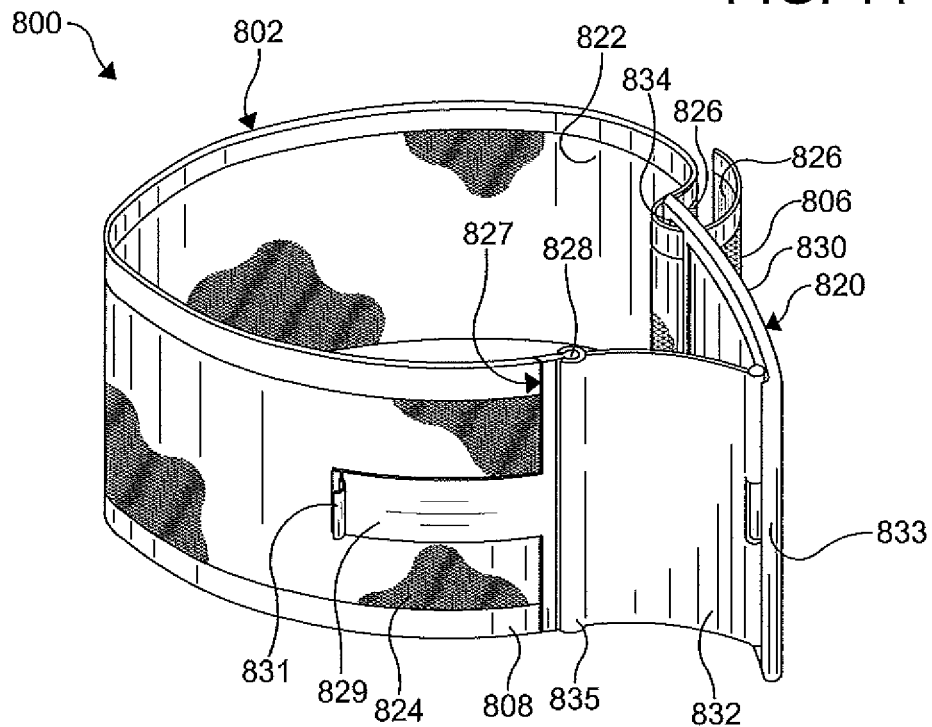
FIG. 15 is a top perspective view of a cuff for a blood pressure measuring system according to another embodiment of the invention, wherein the cuff is in a partially extended position.

FIG. 15 shows a cuff 800 for a blood pressure measuring system (not shown) according to another embodiment of the invention. The cuff 800 includes a flexible elongate band 802 having spaced apart opposing ends 806, 808 and a sizing feature or mechanism 820. It is understood that the band 802 can have any length as desired. The band 802 includes an inner surface 822 and an outer surface 824. Portions of the outer surface 824 are produced from an affixing material 826 such as hook and loop tape, for example. It is understood, however, that the band 802 can be produced from any material as desired. An attachment device 827 is disposed on the end 808 of the band 802. It is understood that the attachment device 827 can be disposed on the end 806 of the band 802 if desired. The attachment device 827 includes a shaft 828 having an elongate member 829 extending laterally outwardly therefrom. The member 829 extends into the end 808 of the band 802 to provide support for the sizing mechanism 820. As illustrated, the member 829 includes a protuberance 831 formed thereon. The protuberance 831 shown has a generally reversed C-shaped cross-section. It is understood that the protuberance 831 can have any cross-sectional shape as desired such as an S-shaped cross-section, for example. An arcuate outer surface of the protuberance 831 faces towards the sizing mechanism 820.

The sizing mechanism 820 includes a clasping mechanism 830 pivotally coupled to a linkage 832. In the embodiment shown, the clasping mechanism 830 includes a receiving portion 833 formed thereon. The receiving portion 833 of the clasping mechanism 830 cooperates with the protuberance 831 of the attachment device 827 to form a connection therebetween. Particularly, the receiving portion 833 receives the protuberance 831 therein. The clasping mechanism 830 further includes a slot 834 formed therein for receiving the end 806 of the band 802 therethrough. It is understood that the end 808 of the band 802 can be disposed through the slot 834 if desired. The linkage 832 shown is pivotable between a first or extended position and a second or retracted position. The linkage 832 includes a receiving portion 835 pivotally coupled to the shaft 828 of the attachment device 827 to secure the sizing mechanism 820 to the band 802. It is understood that the clasping mechanism 830 and the linkage 832 may further include corresponding features such as ribs and grooves, for example, formed thereon to militate against an undesired movement therebetween.

In operation, the linkage 832 of the sizing mechanism 820 is pivoted to the retracted position causing the clasping mechanism 830 to be positioned on a portion of the end 808 of the band 802 having the linkage 832 disposed therebetween. The receiving portion 833 of the clasping mechanism 830 receives the protuberance 831 of the attachment device 827 therein to form the connection therebetween and releasably secure the sizing mechanism 820 in a closed position. Thereafter, a first portion of the end 806 of the band 802 is disposed through the slot 834 of the clasping mechanism 830. The first portion of the end 806 of the band 802 is caused to overlap onto a second portion of the end 806 of the band 802 to form a loop and constrict a diameter of the cuff 800. The diameter of the cuff 800 is constricted until a desired diameter of the cuff 800 is reached. The affixing material 826 disposed on the first portion of the end 806 cooperates with the affixing material 826 disposed on the second portion of the end 806 to maintain the desired diameter of the cuff 800.

After a blood pressure measurement is conducted by the blood pressure measuring system, the linkage 832 of the sizing mechanism 820 is pivoted to the extended position, separating the receiving portion 833 from the protuberance 831 of the attachment device 827 and expanding the diameter of the cuff 800. Once the desired diameter of the cuff 800 is determined during a first blood pressure measurement, the sizing mechanism 820 can be used to expand and constrict the diameter of the cuff 800. The affixing material 826 disposed on the first portion of the end 806 remains in cooperation with the affixing material 826 disposed on the second portion of the end 806 until an adjustment to the desired diameter of the cuff 800 is needed.

Figure 16:
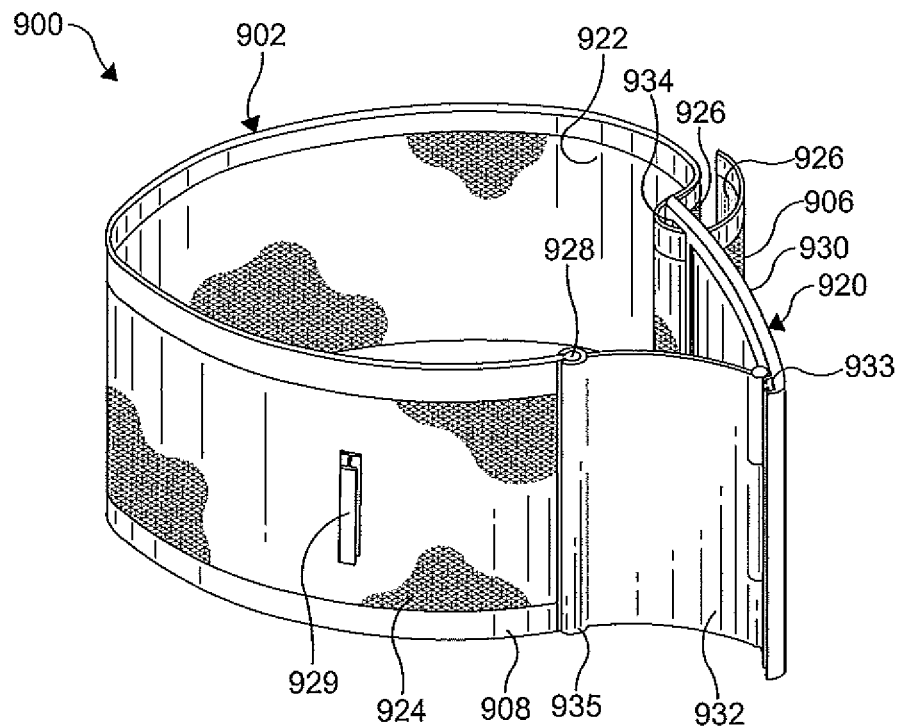
FIG. 16 is a top perspective view of a cuff for a blood pressure measuring system according to another embodiment of the invention, wherein the cuff is in a partially extended position.

FIG. 16 shows a cuff 900 for a blood pressure measuring system (not shown) according to another embodiment of the invention. The cuff 900 includes a flexible elongate band 902 having spaced apart opposing ends 906, 908 and a sizing feature or mechanism 920. It is understood that the band 902 can have any length as desired. The band 902 includes an inner surface 922 and an outer surface 924. Portions of the outer surface 924 are produced from an affixing material 926 such as hook and loop tape, for example. It is understood, however, that the band 902 can be produced from any material as desired. An attachment device 928 is disposed on the end 908 of the band 902. The end 908 of the band 902 further includes a protuberance 929 disposed thereon. Although the protuberance 929 shown has a generally T-shaped cross-section, it is understood that the protuberance 929 can have any cross-sectional shape as desired such as an S-shaped cross-section, for example. It is understood that the attachment device 928 and the protuberance 929 can be disposed on the end 906 of the band 902 if desired.

The sizing mechanism 920 includes a clasping mechanism 930 pivotally coupled to a linkage 932. The clasping mechanism 930 includes a receiving portion 933 formed thereon. In the embodiment shown, the receiving portion 933 has a generally T-shaped cross-section. It is understood that the receiving portion 933 can have any cross-sectional shape as desired such as an S-shaped cross-section, for example. The receiving portion 933 of the clasping mechanism 930 cooperates with the protuberance 929 of the attachment device 928 to form a connection therebetween. Particularly, the receiving portion 933 receives the protuberance 929 therein. The clasping mechanism 930 further includes a slot 934 formed therein for receiving the end 906 therethrough. It is understood that the end 908 can be disposed through the slot 934 if desired. The linkage 932 shown is pivotable between a first or extended position and a second or retracted position. The linkage 932 includes a receiving portion 935 pivotally coupled to the attachment device 928 to secure the sizing mechanism 920 to the band 902. It is understood that the clasping mechanism 930 and the linkage 932 may further include corresponding features such as ribs and grooves, for example, formed thereon to militate against an undesired movement therebetween.

In operation, the linkage 932 of the sizing mechanism 920 is pivoted to the retracted position causing the clasping mechanism 930 to be positioned on a portion of the end 908 of the band 902 having the linkage 932 disposed therebetween. The receiving portion 933 of the clasping mechanism 930 receives the protuberance 929 therein to form the connection therebetween and releasably secure the sizing mechanism 920 in a closed position. Thereafter, a first portion of the end 906 of the band 902 is disposed through the slot 934 of the clasping mechanism 930. The first portion of the end 906 of the band 902 is caused to overlap onto a second portion of the end 906 of the band 902 to form a loop and constrict a diameter of the cuff 900. The diameter of the cuff 900 is constricted until a desired diameter of the cuff 900 is reached. The affixing material 926 disposed on the first portion of the end 906 cooperates with the affixing material 926 disposed on the second portion of the end 906 to maintain the desired diameter of the cuff 900.

After a blood pressure measurement is conducted by the blood pressure measuring system, the linkage 932 of the sizing mechanism 920 is pivoted to the extended position, separating the receiving portion 933 of the linkage 932 from the protuberance 929 and expanding the diameter of the cuff 900. Once the desired diameter of the cuff 900 is determined during a first blood pressure measurement, the sizing mechanism 920 can be used to expand and constrict the diameter of the cuff 900. The affixing material 926 disposed on the first portion of the end 906 remains in cooperation with the affixing material 926 disposed on the second portion of the end 906 until an adjustment to the desired diameter of the cuff 900 is needed.

Figure 17:
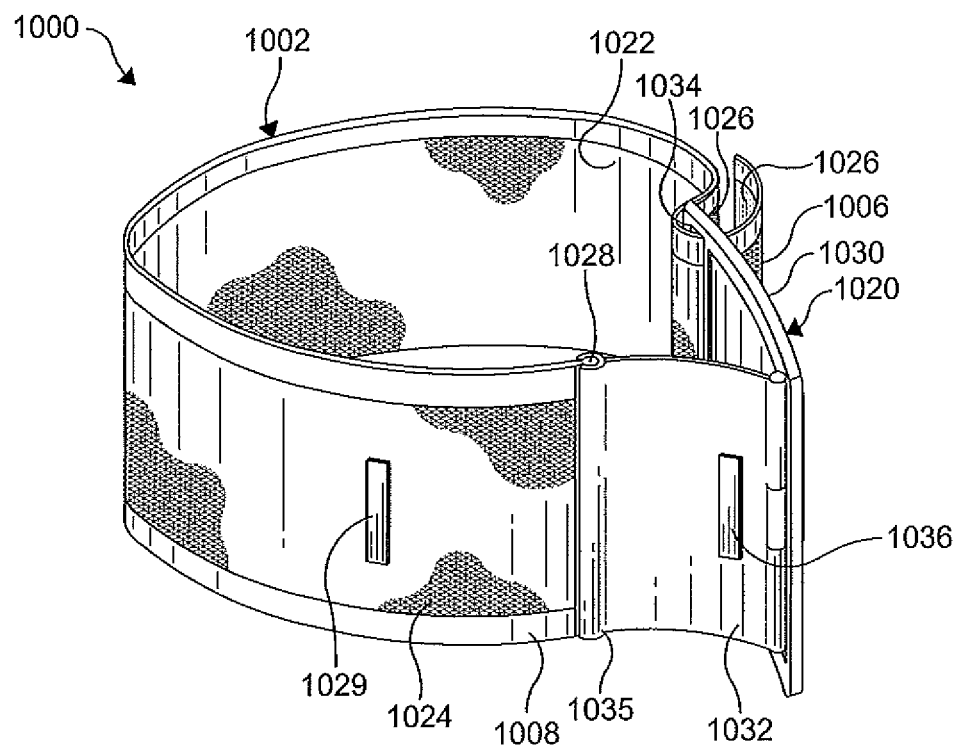
FIG. 17 is a top perspective view of a cuff for a blood pressure measuring system according to another embodiment of the invention, wherein the cuff is in a partially extended position.

FIG. 17 shows a cuff 1000 for a blood pressure measuring system (not shown) according to another embodiment of the invention. The cuff 1000 includes a flexible elongate band 1002 having spaced apart opposing ends 1006, 1008 and a sizing feature or mechanism 1020. It is understood that the band 1002 can have any length as desired. The band 1002 includes an inner surface 1022 and an outer surface 1024. Portions of the outer surface 1024 are produced from an affixing material 1026 such as hook and loop tape, for example. It is understood, however, that the band 1002 can be produced from any material as desired. An attachment device 1028 is disposed on the end 1008 of the band 1002. The end 1008 of the band 1002 further includes a magnetic element 1029 at least partially disposed therein. It is understood that the term "magnetic element" herein represents an element produced from one of a naturally magnetic material, a material capable of being magnetized, and a material attracted by a magnet such as a metal plate, for example. It is further understood that the attachment device 1028 and the magnetic element 1029 can be disposed on the end 1006 of the band 1002 if desired. Although the magnetic element 1029 shown has a generally rectangular shape, it is understood that the magnetic element 1029 can have any shape as desired.

The sizing mechanism 1020 includes a clasping mechanism 1030 pivotally coupled to a linkage 1032. A slot 1034 for receiving the end 1008 therethrough is formed in the clasping mechanism 1030. It is understood that the slot 1034 can receive the end 1006 therethrough if desired. The linkage 1032 shown is pivotable between a first or extended position and a second or retracted position. The linkage 1032 includes a receiving portion 1035 pivotally coupled to the attachment device 1028 to secure the sizing mechanism 1020 to the band 1002. The linkage 1032 further includes a magnetic element 1036 at least partially disposed therein. The magnetic element 1036 cooperates with the magnetic element 1029 disposed in the band 1002 to form a magnetic connection therebetween. It is understood that the clasping mechanism 1030 and the linkage 1032 may further include corresponding features such as ribs and grooves, for example, formed thereon to militate against an undesired movement therebetween.

In operation, the linkage 1032 of the sizing mechanism 1020 is pivoted to the retracted position causing the clasping mechanism 1030 to be positioned on a portion of the end 1008 of the band 1002 having the linkage 1032 disposed therebetween. The magnetic element 1036 disposed in the linkage 1032 cooperates with the magnetic element 1029 disposed in the band 1002 to form the magnetic connection therebetween and releasably secure the sizing mechanism 1020 in a closed position. Thereafter, a first portion of the end 1006 of the band 1002 is disposed through the slot 1034 of the clasping mechanism 1030. The first portion of the end 1006 of the band 1002 is caused to overlap onto a second portion of the end 1006 of the band 1002 to form a loop and constrict a diameter of the cuff 1000. The diameter of the cuff 1000 is constricted until a desired diameter of the cuff 1000 is reached. The affixing material 1026 disposed on the first portion of the end 1006 cooperates with the affixing material 1026 disposed on the second portion of the end 1006 to maintain the desired diameter of the cuff 1000.

After a blood pressure measurement is conducted by the blood pressure measuring system, the linkage 1032 of the sizing mechanism 1020 is pivoted to the extended position, separating the magnetic element 1036 from the magnetic element 1029 and expanding the diameter of the cuff 1000. Once the desired diameter of the cuff 1000 is determined during a first blood pressure measurement, the sizing mechanism 1020 can be used to expand and constrict the diameter of the cuff 1000. The affixing material 1026 disposed on the first portion of the end 1006 remains in cooperation with the affixing material 1026 disposed on the second portion of the end 1006 until an adjustment to the desired diameter of the cuff 1000 is needed.

Figure 18:
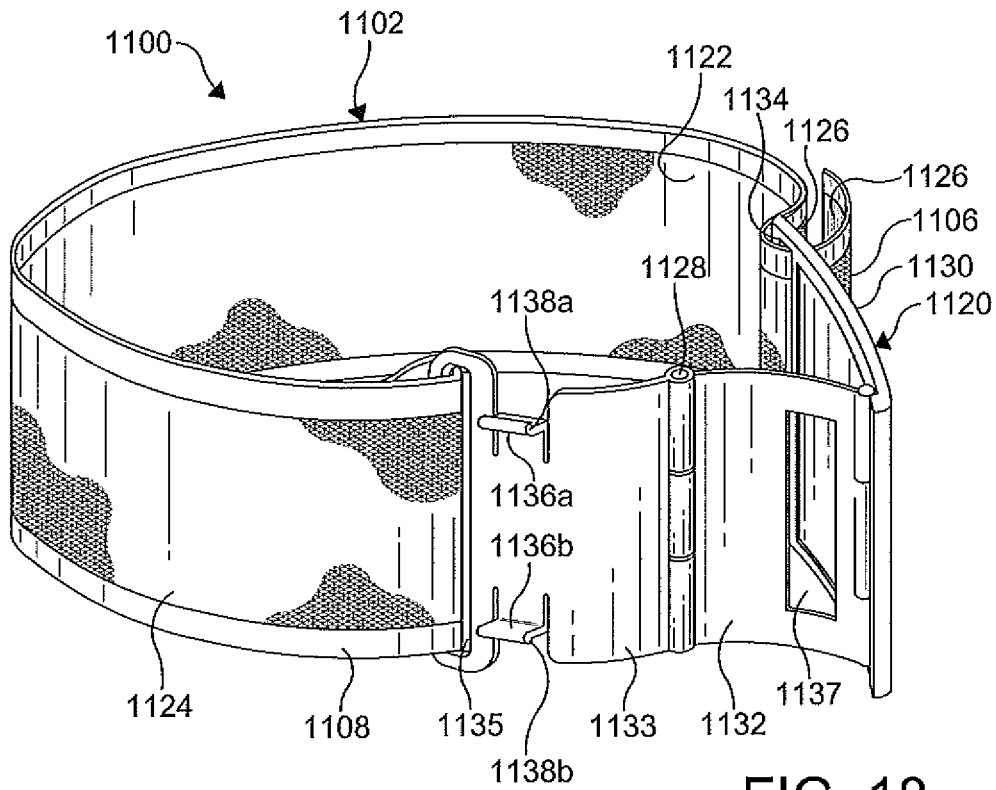
FIG. 18 is a top perspective view of a cuff for a blood pressure measuring system according to another embodiment of the invention, wherein the cuff is in a partially extended position.

FIG. 18 shows a cuff 1100 for a blood pressure measuring system (not shown) according to another embodiment of the invention. The cuff 1100 includes a flexible elongate band 1102 having spaced apart opposing ends 1106, 1108 and a sizing feature or mechanism 1120. It is understood that the band 1102 can have any length as desired. The band 1102 includes an inner surface 1122 and an outer surface 1124. As illustrated, portions of the outer surface 1124 are produced from an affixing material 1126 such as hook and loop tape, for example. It is understood, however, that the band 1102 can be produced from any material as desired.

As shown, the sizing mechanism 1120 includes a clasping mechanism 1130 and a pair of linkages 1132, 1133. It is understood that the sizing mechanism 1120 can be produced from any material as desired such as a plastic material, for example. A slot 1134 for receiving one of the ends 1106, 1108 therethrough is formed in the clasping mechanism 1130. The clasping mechanism 1130 is pivotally coupled to the linkage 1132. The linkage 1132 is pivotable between a first or extended position and a second or retracted position. The linkage 1133 is pivotally coupled to the linkage 1132 and one of the ends 1106, 1108 of the band 1102. The linkage 1133 includes a slot 1135 for receiving one of the ends 1106, 1108 therethrough. As shown, a first portion of the end 1108 of the band 1102 is disposed through the slot 1135 of the linkage 1133 and caused to overlap onto a second portion of the end 1108 to form a loop. The first portion of the end 1108 of the band 1102 is secured to the second portion of the end 1108 by any method as desired such as by an adhesive, stitches, fasteners, and the like, for example. It is understood that the linkage 1133 can be coupled to the end 1106 of the band 1102 if desired. It is further understood that the linkage 1133 can be coupled to one of the ends 1106, 1108 by any means as desired such as by an attachment mechanism, adhesive, and any combination thereof, for example.

As shown, the linkage 1133 includes a pair of spaced apart protuberances 1136a, 1136b formed thereon. An aperture 1137 formed in the linkage 1132 receives the protuberances 1136a, 1136b therein. The protuberances 1136a, 1136b are releasably secured in aperture 1137 of the linkage 1132 by respective shoulder portions 1138a, 1138b formed on the protuberances 1136a, 1136b. The shoulder portions 1138a, 1138b cooperate with portions of the linkage 1132 adjacent the aperture 1137 to form a connection therebetween. The protuberances 1136a, 1136b are flexible to facilitate a release thereof from the linkage 1132. It is understood that the clasping mechanism 1130 and the linkages 1132, 1133 may further include corresponding features such as ribs and grooves, for example, formed thereon to militate against an undesired movement therebetween.

In operation, the linkage 1132 is pivoted to the retracted position. The clasping mechanism 1130 is then urged in a first direction and positioned on the linkage 1133 having the linkage 1132 disposed therebetween. The protuberances 1136a, 1136b of the linkage 1133 are received through the aperture 1137 formed in the linkage 1132. The shoulder portions 1138a, 1138b of the protuberances 1136a, 1136b cooperate with the portions of the linkage 1132 adjacent the aperture 1137 to form the connection therebetween and releasably secure the sizing mechanism 1120 in a closed position. Thereafter, a first portion of the end 1106 of the band 1102 is disposed through the slot 1134 of the clasping mechanism 1130. The first portion of the end 1106 of the band 1102 is caused to overlap onto a second portion of the end 1106 of the band 1102 to form a loop and constrict a diameter of the cuff 1100. The diameter of the cuff 1100 is constricted until a desired diameter of the cuff 1100 is reached. The affixing material 1126 disposed on the first portion of the end 1106 cooperates with the affixing material 1126 disposed on the second portion of the end 1106 to maintain the desired diameter of the cuff 1100.

After a blood pressure measurement is conducted by the blood pressure measuring system, the clasping mechanism 1130 of the sizing mechanism 1120 is urged outward away from the band 1102. The protuberances 1136a, 1136b are then flexed inwardly, releasing the shoulder portions 1138a, 1138b from the linkage 1132. The protuberances 1136a, 1136b are caused to be received through the aperture 1137 and urged away from the linkage 1132. The clasping mechanism 1130 is then urged in a second direction causing a pivoting of the linkage 1132 to the extended position and expanding the diameter of the cuff 1100. Once the desired diameter of the cuff 1100 is determined during a first blood pressure measurement, the sizing mechanism 1120 can be used to expand and constrict the diameter of the cuff 1100. The affixing material 1126 disposed on the first portion of the end 1106 remains in cooperation with the affixing material 1126 disposed on the second portion of the end 1106 until an adjustment to the desired diameter of the cuff 1100 is needed.

Figure 19:
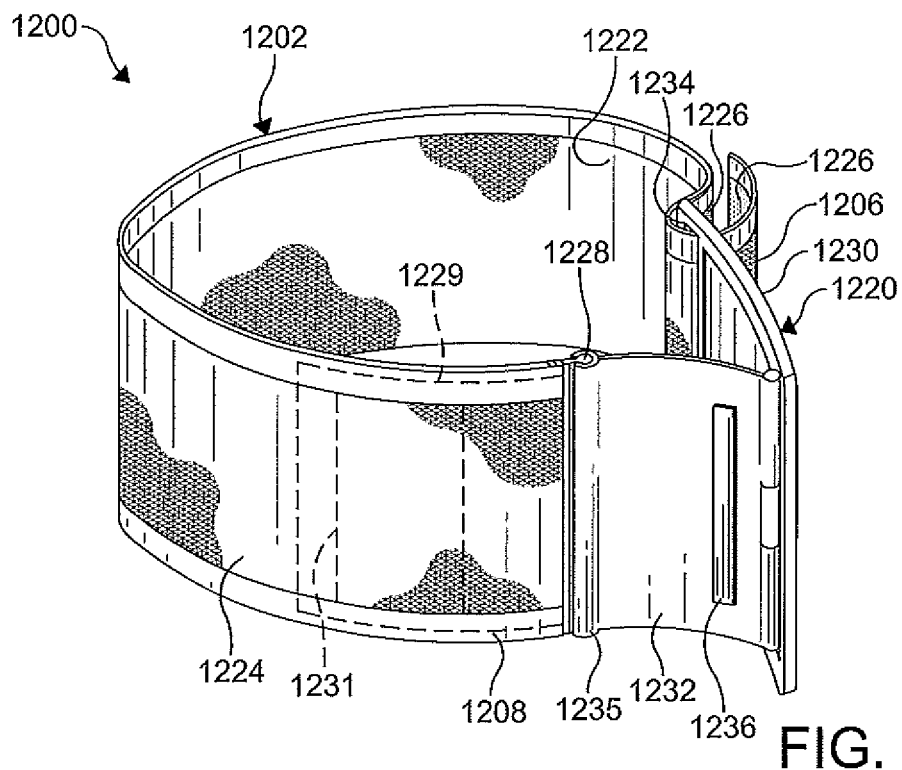
FIG. 19 is a top perspective view of a cuff for a blood pressure measuring system according to another embodiment of the invention, wherein the cuff is in a partially extended position.

FIG. 19 shows a cuff 1200 for a blood pressure measuring system (not shown) according to another embodiment of the invention. The cuff 1200 includes a flexible elongate band 1202 having spaced apart opposing ends 1206, 1208 and a sizing feature or mechanism 1220. It is understood that the band 1202 can have any length as desired. The band 1202 includes an inner surface 1222 and an outer surface 1224. Portions of the outer surface 1224 are produced from an affixing material 1226 such as hook and loop tape, for example. It is understood, however, that the band 1202 can be produced from any material as desired. An attachment device 1228 is disposed on the end 1208 of the band 1202. It is understood that the attachment device 1228 can be disposed on the end 1206 of the band 1202 if desired. As illustrated, a portion 1229 of the attachment device 1228, as indicated by dashed lines in FIG. 19, is disposed in the end 1208 of the 1202 to provide support thereto. The end 1208 of the band 1202 further includes a magnetic element 1231 at least partially disposed therein. Although the magnetic element 1231 shown has a generally rectangular shape, it is understood that the magnetic element 1231 can have any shape as desired.

The sizing mechanism 1220 includes a clasping mechanism 1230 pivotally coupled to a linkage 1232. A slot 1234 for receiving the end 1208 therethrough is formed in the clasping mechanism 1230. It is understood that the slot 1234 can receive the end 1206 therethrough if desired. The linkage 1232 shown is pivotable between a first or extended position and a second or retracted position. The linkage 1232 includes a receiving portion 1235 pivotally coupled to the attachment device 1228 to secure the sizing mechanism 1220 to the band 1202. The linkage 1232 further includes a magnetic element 1236 at least partially disposed therein. The magnetic element 1236 cooperates with the magnetic element 1231 disposed in the band 1202 to form a magnetic connection therebetween. It is understood that the clasping mechanism 1230 and the linkage 1232 may further include corresponding features such as ribs and grooves, for example, formed thereon to militate against an undesired movement therebetween.

In operation, the linkage 1232 of the sizing mechanism 1220 is pivoted to the retracted position causing the clasping mechanism 1230 to be positioned on a portion of the end 1208 of the band 1202 having the linkage 1232 disposed therebetween. The magnetic element 1236 disposed in the linkage 1232 cooperates with the magnetic element 1231 disposed in the band 1202 to form the magnetic connection therebetween and releasably secure the sizing mechanism 1220 in a closed position. Thereafter, a first portion of the end 1206 of the band 1202 is disposed through the slot 1234 of the clasping mechanism 1230. The first portion of the end 1206 of the band 1202 is caused to overlap onto a second portion of the end 1206 of the band 1202 to form a loop and constrict a diameter of the cuff 1200. The diameter of the cuff 1200 is constricted until a desired diameter of the cuff 1200 is reached. The affixing material 1226 disposed on the first portion of the end 1206 cooperates with the affixing material 1226 disposed on the second portion of the end 1206 to maintain the desired diameter of the cuff 1200.

After a blood pressure measurement is conducted by the blood pressure measuring system, the linkage 1232 of the sizing mechanism 1220 is pivoted to the extended position, separating the magnetic element 1236 from the magnetic element 1229 and expanding the diameter of the cuff 1200. Once the desired diameter of the cuff 1200 is determined during a first blood pressure measurement, the sizing mechanism 1220 can be used to expand and constrict the diameter of the cuff 1200. The affixing material 1226 disposed on the first portion of the end 1206 remains in cooperation with the affixing material 1226 disposed on the second portion of the end 1206 until an adjustment to the desired diameter of the cuff 1200 is needed.

Figure 20:
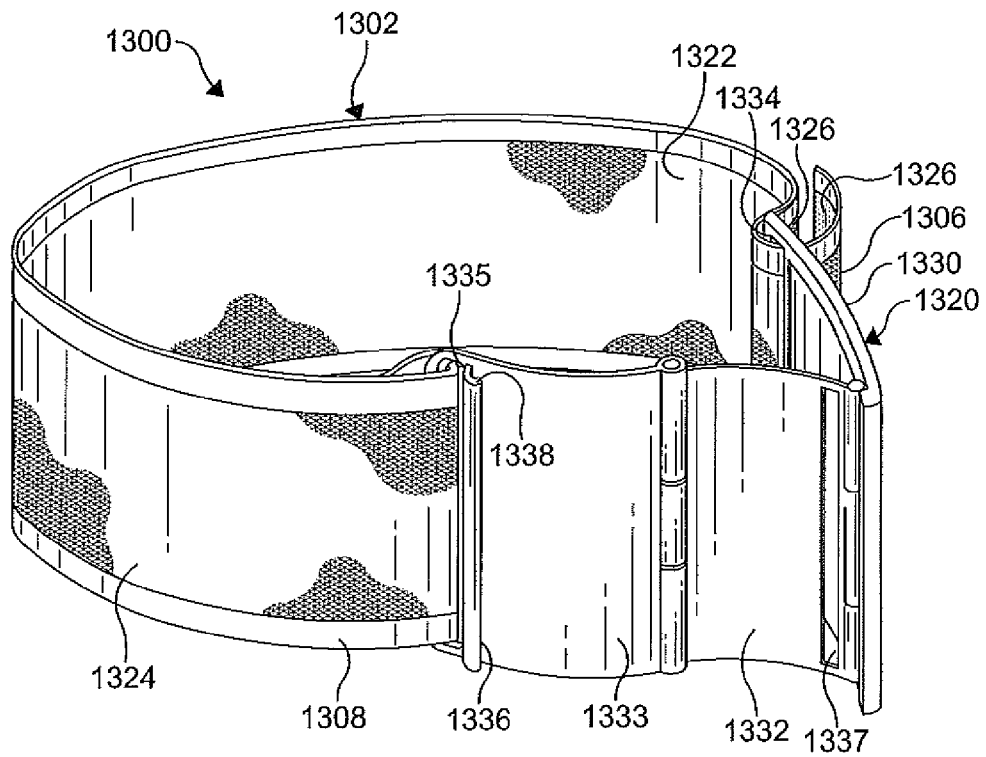
FIG. 20 is a top perspective view of a cuff for a blood pressure measuring system according to another embodiment of the invention, wherein the cuff is in a partially extended position.

FIG. 20 shows a cuff 1300 for a blood pressure measuring system (not shown) according to another embodiment of the invention. The cuff 1300 includes a flexible elongate band 1302 having spaced apart opposing ends 1306, 1308 and a sizing feature or mechanism 1320. It is understood that the band 1302 can have any length as desired. The band 1302 includes an inner surface 1322 and an outer surface 1324. As illustrated, portions of the outer surface 1324 are produced from an affixing material 1326 such as hook and loop tape, for example. It is understood, however, that the band 1302 can be produced from any material as desired.

As shown, the sizing mechanism 1320 includes a clasping mechanism 1330 and a pair of linkages 1332, 1333. It is understood that the sizing mechanism 1320 can be produced from any material as desired such as a plastic material, for example. A slot 1334 for receiving one of the ends 1306, 1308 therethrough is formed in the clasping mechanism 1330. The clasping mechanism 1330 is pivotally coupled to the linkage 1332. The linkage 1332 is pivotable between a first or extended position and a second or retracted position.

The linkage 1333 is pivotally coupled to the linkage 1332 and one of the ends 1306, 1308 of the band 1302. The linkage 1333 includes a slot 1335 for receiving one of the ends 1306, 1308 therethrough. As shown, a first portion of the end 1308 of the band 1302 is disposed through the slot 1335 of the linkage 1333 and caused to overlap onto a second portion of the end 1308 to form a loop. The first portion of the end 1308 of the band 1302 is secured to the second portion thereof by any means as desired such as by an adhesive, stitches, fasteners, and the like, for example. It is understood that the linkage 1333 can be coupled to the end 1306 of the band 1302 if desired. It is further understood that the linkage 1333 can be coupled to one of the ends 1306, 1308 by any means as desired such as by an attachment mechanism, adhesive, and any combination thereof, for example.

As shown, the linkage 1333 includes a protuberance 1336 formed thereon. An aperture 1337 formed in the linkage 1332 receives the protuberance 1336 therein. The protuberance 1336 is releasably secured in aperture 1337 of the linkage 1332 by a shoulder portion 1338 formed on the protuberance 1336. The shoulder portion 1338 cooperates with a portion of the linkage 1332 adjacent the aperture 1337 to form a connection therebetween. The protuberance 1336 is flexible to facilitate a release thereof from the linkage 1332. It is understood that the clasping mechanism 1330 and the linkages 1332, 1333 may further include corresponding features such as ribs and grooves, for example, formed thereon to militate against an undesired movement therebetween.

In operation, the linkage 1332 is pivoted to the retracted position. The clasping mechanism 1330 is then urged in a first direction and positioned on the linkage 1333 having the linkage 1332 disposed therebetween. The protuberance 1336 of the linkage 1333 is received through the aperture 1337 formed in the linkage 1332. The shoulder portion 1338 of the protuberance 1336 cooperates with the portion of the linkage 1332 adjacent the aperture 1337 to form the connection therebetween and releasably secure the sizing mechanism 1320 in a closed position. Thereafter, a first portion of the end 1306 of the band 1302 is disposed through the slot 1334 of the clasping mechanism 1330. The first portion of the end 1306 of the band 1302 is caused to overlap onto a second portion of the end 1306 of the band 1302 to form a loop and constrict a diameter of the cuff 1300. The diameter of the cuff 1300 is constricted until a desired diameter of the cuff 1300 is reached. The affixing material 1326 disposed on the first portion of the end 1306 cooperates with the affixing material 1326 disposed on the second portion of the end 1306 to maintain the desired diameter of the cuff 1300.

After a blood pressure measurement is conducted by the blood pressure measuring system, the clasping mechanism 1330 of the sizing mechanism 1320 is urged outward away from the band 1302. The protuberance 1336 is then flexed and urged away from the portion of the linkage 1332 adjacent the aperture 1337, releasing the shoulder portion 1338 from the linkage 1132. The protuberance 1336 is then caused to be received through the aperture 1337 and urged away from the linkage 1332. The clasping mechanism 1330 is urged in a second direction causing a pivoting of the linkage 1332 to the extended position and expanding the diameter of the cuff 1300. Once the desired diameter of the cuff 1300 is determined during a first blood pressure measurement, the sizing mechanism 1320 can be used to expand and constrict the diameter of the cuff 1300. The affixing material 1326 disposed on the first portion of the end 1306 remains in cooperation with the affixing material 1326 disposed on the second portion of the end 1306 until an adjustment to the desired diameter of the cuff 1300 is needed.

Figure 21:
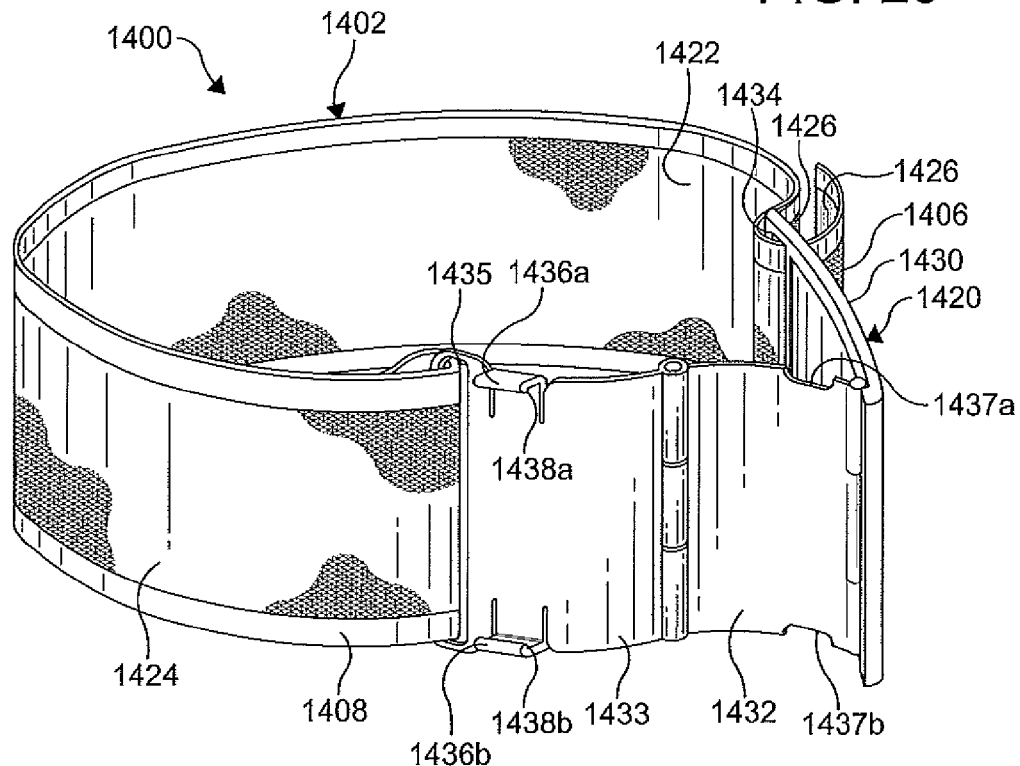
FIG. 21 is a top perspective view of a cuff for a blood pressure measuring system according to another embodiment of the invention, wherein the cuff is in a partially extended position.

FIG. 21 shows a cuff 1400 for a blood pressure measuring system (not shown) according to another embodiment of the invention. The cuff 1400 includes a flexible elongate band 1402 having spaced apart opposing ends 1406, 1408 and a sizing feature or mechanism 1420. It is understood that the band 1402 can have any length as desired. The band 1402 includes an inner surface 1422 and an outer surface 1424. As illustrated, portions of the outer surface 1424 are produced from an affixing material 1426 such as hook and loop tape, for example. It is understood, however, that the band 1402 can be produced from any material as desired.

As shown, the sizing mechanism 1420 includes a clasping mechanism 1430 and a pair of linkages 1432, 1433. It is understood that the sizing mechanism 1420 can be produced from any material as desired such as a plastic material, for example. A slot 1434 for receiving one of the ends 1406, 1408 therethrough is formed in the clasping mechanism 1430. The clasping mechanism 1430 is pivotally coupled to the linkage 1432. The linkage 1432 is pivotable between a first or extended position and a second or retracted position.

The linkage 1433 is pivotally coupled to the linkage 1432 and one of the ends 1406, 1408 of the band 1402. The linkage 1433 includes a slot 1435 for receiving one of the ends 1406, 1408 therethrough. As shown, a first portion of the end 1408 of the band 1402 is disposed through the slot 1435 of the linkage 1433 and caused to overlap onto a second portion of the end 1408 to form a loop. The first portion of the end 1408 of the band 1402 is secured to the second portion of the end 1408 by any means as desired such as by an adhesive, stitches, fasteners, and the like, for example. It is understood that the linkage 1433 can be pivotally coupled to the end 1406 of the band 1402 if desired. It is further understood that the linkage 1433 can be coupled to one of the ends 1406, 1408 by any means as desired such as by an attachment mechanism, adhesive, and any combination thereof, for example.

As shown, the linkage 1433 includes a pair of spaced apart protuberances 1436*a*, 1436*b* formed thereon. The protuberances 1436*a*, 1436*b* include respective shoulder portions 1438a, 1438b formed therein. Corresponding indentations 1437a, 1437b are formed in the linkage 1432 to receive the protuberances 1436a, 1436b therein. The protuberances 1436a, 1436b are releasably secured in the indentations 1437a, 1437b of the linkage 1432 by the shoulder portions 1438a, 1438b formed thereon. The shoulder portions 1438a, 1438b cooperate with portions of the linkage 1432 adjacent the indentations 1437a, 1437b to form a connection therebetween. The protuberances 1436a, 1436b are flexible to facilitate a release thereof from the linkage 1432. It is understood that the clasping mechanism 1430 and the linkages 1432, 1433 may further include corresponding features such as ribs and grooves, for example, formed thereon to militate against an undesired movement therebetween.

In operation, the linkage 1432 is pivoted to the retracted position. The clasping mechanism 1430 is then urged in a first direction and positioned on the linkage 1433 having the linkage 1432 disposed therebetween. The protuberances 1436a, 1436b of the linkage 1433 are received in the corresponding indentations 1437a, 1437b formed in the linkage 1432. The shoulder portions 1438a, 1438b of the protuberances 1436a, 1436b cooperate with the portions of the linkage 1432 adjacent the indentations 1437a, 1437b to form the connection therebetween and releasably secure the sizing mechanism 1420 in a closed position. Thereafter, a first portion of the end 1406 of the band 1402 is disposed through the slot 1434 of the clasping mechanism 1430. The first portion of the end 1406 of the band 1402 is caused to overlap onto a second portion of the end 1406 of the band 1402 to form a loop and constrict a diameter of the cuff 1400. The diameter of the cuff 1400 is constricted until a desired diameter of the cuff 1400 is reached. The affixing material 1426 disposed on the first portion of the end 1406 cooperates with the affixing material 1426 disposed on the second portion of the end 1406 to maintain the desired diameter of the cuff 1400.

After a blood pressure measurement is conducted by the blood pressure measuring system, the clasping mechanism 1430 of the sizing mechanism 1420 is urged outward away from the band 1402. The protuberances 1436a, 1436h are then flexed outwardly, releasing the shoulder portions 1438a, 1438b from the linkage 1432. The protuberances 1436a, 1436b are then urged away from the linkage 1432. Thereafter, the clasping mechanism 1430 is urged in a second direction causing a pivoting of the linkage 1432 to the extended position and expanding the diameter of the cuff 1400. Once the desired diameter of the cuff 1400 is determined during a first blood pressure measurement, the sizing mechanism 1420 can be used to expand and constrict the diameter of the cuff 1400. The affixing material 1426 disposed on the first portion of the end 1406 remains in cooperation with the affixing material 1426 disposed on the second portion of the end 1406 until an adjustment to the desired diameter of the cuff 1400 is needed.

Figure 22:
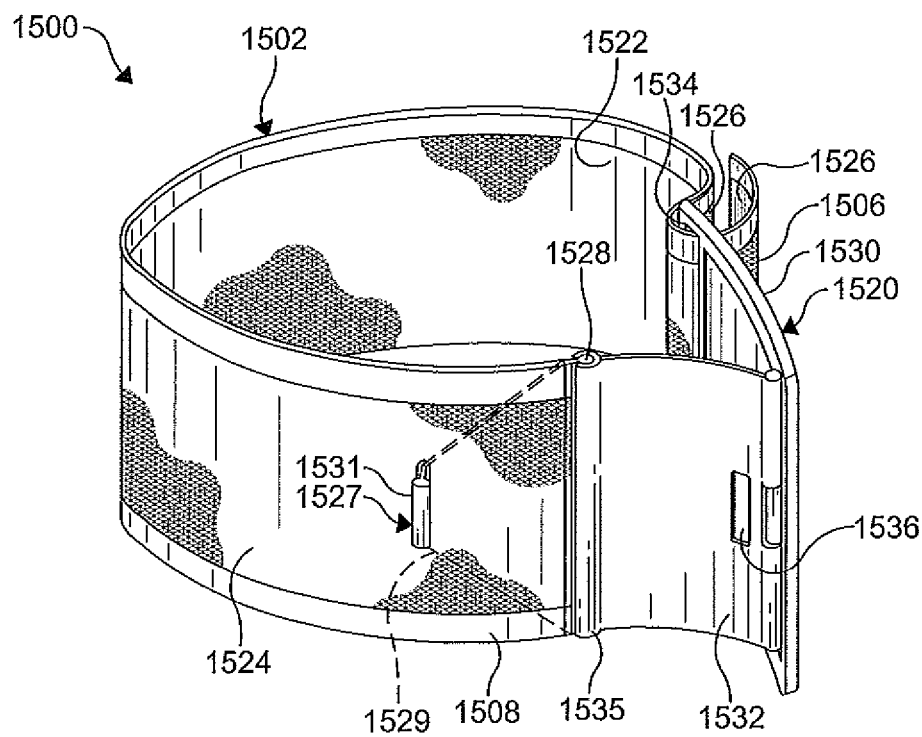
FIG. 22 is a top perspective view of a cuff for a blood pressure measuring system according to another embodiment of the invention, wherein the cuff is in a partially extended position.

FIG. 22 shows a cuff 1500 for a blood pressure measuring system (not shown) according to another embodiment of the invention. The cuff 1500 includes a flexible elongate band 1502 having spaced apart opposing ends 1506, 1508 and a sizing feature or mechanism 1520. It is understood that the band 1502 can have any length as desired. The band 1502 includes an inner surface 1522 and an outer surface 1524. Portions of the outer surface 1524 are produced from an affixing material 1526 such as hook and loop tape, for example. It is understood, however, that the band 1502 can be produced from any material as desired. An attachment device 1527 is disposed on the end 1508 of the band 1502. The attachment device 1527 includes a shaft 1528 having a support member 1529 extending laterally outwardly therefrom. The member 1529 extends into the end 1508 of the band 1502 to provide support for the sizing mechanism 1520. As illustrated, the support member 1529 includes a protuberance 1531 formed thereon. The protuberance 1531 shown has a generally circular cross-sectional shape. It is understood that the protuberance 1531 can have any cross-sectional shape as desired such as an S-shaped cross-section, for example. It is understood that the attachment device 1527 can be disposed on the end 1506 of the band 1502 if desired.

The sizing mechanism 1520 includes a clasping mechanism 1530 pivotally coupled to a linkage 1532. The clasping mechanism 1530 includes a slot 1534 formed therein for receiving the end 1506 therethrough. It is understood that the end 1508 can be disposed through the slot 1534 if desired. The linkage 1532 shown is pivotable between a first or extended position and a second or retracted position. The linkage 1532 includes a receiving portion 1535 pivotally coupled to the shaft 1528 of the attachment device 1527. In the embodiment shown, the linkage 1532 further includes a corresponding aperture 1536 formed therein. The aperture 1536 receives the protuberance 1531 of the attachment device 1527 therein to form an interference fit therebetween. It is understood that the clasping mechanism 1530 and the linkage 1532 may further include corresponding features such as ribs and grooves, for example, formed thereon to militate against an undesired movement therebetween.

In operation, the linkage 1532 of the sizing mechanism 1520 is pivoted to the retracted position causing the clasping mechanism 1530 to be positioned on a portion of the end 1508 of the band 1502 having the linkage 1532 disposed therebetween. The aperture 1536 of the linkage 1532 receives the protuberance 1531 of the attachment device 1527 therein to form the interference fit therebetween and releasably secure the sizing mechanism 1520 in a closed position. Thereafter, a first portion of the end 1506 of the band 1502 is disposed through the slot 1534 of the clasping mechanism 1530. The first portion of the end 1506 of the band 1502 is caused to overlap onto a second portion of the end 1506 of the band 1502 to form a loop and constrict a diameter of the cuff 1500. The diameter of the cuff 1500 is constricted until a desired diameter of the cuff 1500 is reached. The affixing material 1526 disposed on the first portion of the end 1506 cooperates with the affixing material 1526 disposed on the second portion of the end 1506 to maintain the desired diameter of the cuff 1500.

After a blood pressure measurement is conducted by the blood pressure measuring system, the linkage 1532 of the sizing mechanism 1520 is pivoted to the extended position, separating the linkage 1532 from the protuberance 1531 of the attachment device 1527 and expanding the diameter of the cuff 1500. Once the desired diameter of the cuff 1500 is determined during a first blood pressure measurement, the sizing mechanism 1520 can be used to expand and constrict the diameter of the cuff 1500. The affixing material 1526 disposed on the first portion of the end 1506 remains in cooperation with the affixing material 1526 disposed on the second portion of the end 1506 until an adjustment to the desired diameter of the cuff 1500 is needed.

Figure 23:
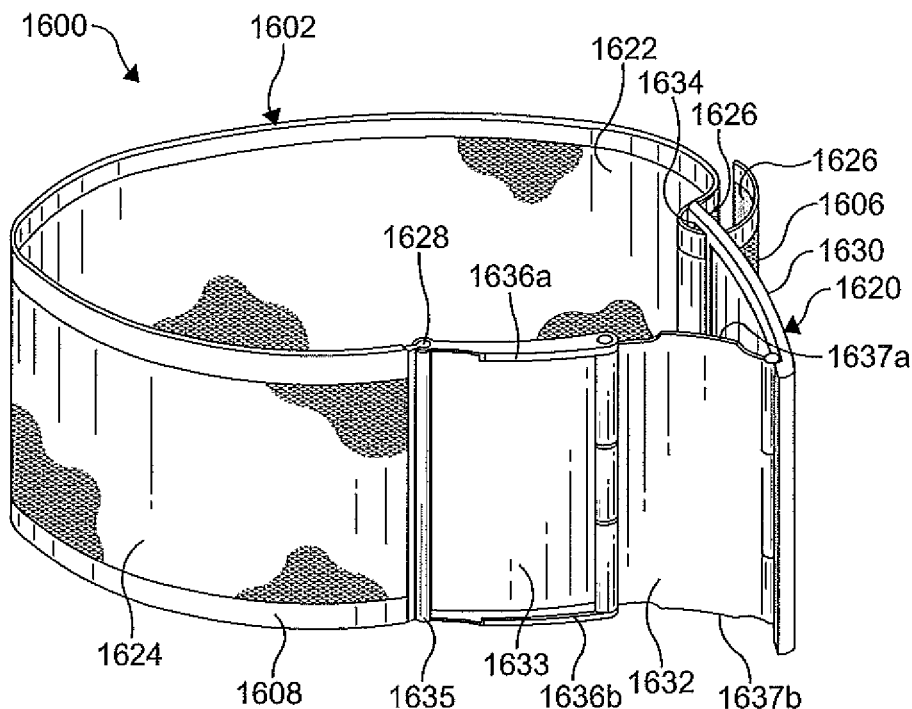
FIG. 23 is a top perspective view of a cuff for a blood pressure measuring system according to another embodiment of the invention, wherein the cuff is in a partially extended position.

FIG. 23 shows a cuff 1600 for a blood pressure measuring system (not shown) according to another embodiment of the invention. The cuff 1600 includes a flexible elongate band 1602 having spaced apart opposing ends 1606, 1608 and a sizing feature or mechanism 1620. It is understood that the band 1602 can have any length as desired. The band 1602 includes an inner surface 1622 and an outer surface 1624. As illustrated, portions of the outer surface 1624 are produced from an affixing material 1626 such as hook and loop tape, for example. It is understood, however, that the band 1602 can be produced from any material as desired. An attachment device 1628 is disposed on the end 1608 of the band 1602. It is understood that the attachment device 1628 can be disposed on the end 1606 of the band 1602 if desired.

As shown, the sizing mechanism 1620 includes a clasping mechanism 1630 and a pair of linkages 1632, 1633. It is understood that the sizing mechanism 1620 can be produced from any material as desired such as a plastic material, for example. A slot 1634 for receiving one of the ends 1606, 1608 therethrough is formed in the clasping mechanism 1630. The clasping mechanism 1630 is pivotally coupled to the linkage 1632. The linkage 1632 is pivotable between a first or extended position and a second or retracted position.

The linkage 1633 is pivotally coupled to the linkage 1632 and one of the ends 1606, 1608 of the band 1602. The linkage 1633 includes a receiving portion 1635 pivotally coupled to the attachment device 1628 disposed on the end 1608 of the band 1602 to secure the sizing mechanism 1620 to the band 1602. It is understood that the linkage 1633 can be pivotally coupled to the end 1606 of the band 1602 if desired. It is further understood that the linkage 1633 can be coupled to one of the ends 1606, 1608 by any means as desired such as by an attachment mechanism, adhesive, and any combination thereof, for example.

As shown, the linkage 1633 includes a pair of spaced apart channels 1636a, 1636b formed thereon. Corresponding tabs 1637a, 1637b are formed on the linkage 1632. The tabs 1637a, 1637b are received in the channels 1636a, 1636b to form a connection therebetween and releasably secure the sizing mechanism 1620 in a closed position. It is understood that the clasping mechanism 1630 and the linkages 1632, 1633 may further include corresponding features such as ribs and grooves, for example, formed thereon to militate against an undesired movement therebetween.

In operation, the linkage 1632 is pivoted to the retracted position. The clasping mechanism 1630 is then urged in a first direction and positioned on the linkage 1633 having the linkage 1632 disposed therebetween. The tabs 1637a, 16376 of the linkage 1632 are received in the corresponding channels 1636a, 1636b formed on the linkage 1633 to form the connection therebetween and releasably secure the sizing mechanism 1620 in the closed position. Thereafter, a first portion of the end 1606 of the band 1602 is disposed through the slot 1634 of the clasping mechanism 1630. The first portion of the end 1606 of the band 1602 is caused to overlap onto a second portion of the end 1606 of the band 1602 to form a loop and constrict a diameter of the cuff 1600. The diameter of the cuff 1600 is constricted until a desired diameter of the cuff 1600 is reached. The affixing material 1626 disposed on the first portion of the end 1606 cooperates with the affixing material 1626 disposed on the second portion of the end 1606 to maintain the desired diameter of the cuff 1600.

After a blood pressure measurement is conducted by the blood pressure measuring system, the clasping mechanism 1630 of the sizing mechanism 1620 is urged outward away from the band 1602. Accordingly, the tabs 1637a, 1637b of the linkage 1632 are caused to be released from the channels 1636a, 1636b of the linkage 1633. The clasping mechanism 1630 is then urged in a second direction causing a pivoting of the linkage 1632 to the extended position and expanding the diameter of the cuff 1600. Once the desired diameter of the cuff 1600 is determined during a first blood pressure measurement, the sizing mechanism 1620 can be used to expand and constrict the diameter of the cuff 1600. The affixing material 1626 disposed on the first portion of the end 1606 remains in cooperation with the affixing material 1626 disposed on the second portion of the end 1606 until an adjustment to the desired diameter of the cuff 1600 is needed.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A blood pressure measuring system comprising:
a cuff for receiving an arm of a user, the cuff having a flexible elongate band including a first end and a second end spaced from the first end, the band having an inner surface and an outer surface;
an affixing material provided on a first portion of the outer surface of the first end of the band and on a second portion of the outer surface of the first end of the band;
a sizing mechanism coupled to at least one of the first end and the second end of the band to selectively expand and constrict a diameter of the band around the arm for conducting a blood pressure measurement with the blood pressure measuring system, the sizing mechanism including a clasping mechanism pivotably coupled to a first linkage and a second linkage pivotably coupled to the first linkage; wherein the second linkage is pivotably coupled to one of the first end or the second end, clasping mechanism including a slot for receiving the first end of the band to allow the first portion and the second portion of the band outer surface to cooperate to form a loop; and
an actuator to release the sizing mechanism from a closed position and cause the diameter of the band to expand after conducting the blood pressure measurement with the blood pressure measuring system.

2. The system according to claim 1, wherein the first linkage is pivotable between an extended position and a retracted position.

3. The system according to claim 1, wherein the second linkage includes a protuberance formed thereon which cooperates with the clasping mechanism to releasably secure the sizing mechanism in the closed position.

4. The system according to claim 1, wherein the actuator includes a pivotable mechanism coupled to the protuberance to cause a release of the clasping mechanism therefrom.

5. The system according to claim 1, wherein the second linkage includes a latch and the clasping mechanism includes an indentation for receiving the latch.

6. The system according to claim 1, wherein the second linkage includes a pair of spaced apart channels to receive the first linkage therebetween.

7. The system according to claim 1, wherein the sizing mechanism is releasably secured in the closed position by a magnetic connection.

* * * * *

UNITED STATES PATENT AND TRADEMARK OFFICE
CERTIFICATE OF CORRECTION

PATENT NO. : 9,706,932 B2
APPLICATION NO. : 13/576021
DATED : July 18, 2017
INVENTOR(S) : Robert T. McCulloch et al.

Page 1 of 1

It is certified that error appears in the above-identified patent and that said Letters Patent is hereby corrected as shown below:

In the Claims

Column 24, Line 36, Claim 1:
After "or the second end,"
Insert -- the --

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*